United States Patent [19]
Branham et al.

[11] Patent Number: 5,687,737
[45] Date of Patent: Nov. 18, 1997

[54] COMPUTERIZED THREE-DIMENSIONAL CARDIAC MAPPING WITH INTERACTIVE VISUAL DISPLAYS

[75] Inventors: Barry H. Branham, Ballwin; James L. Cox; John P. Boineau, both of Ladue; Richard B. Schuessler, Ballwin, all of Mo.

[73] Assignee: Washington University, St. Louis, Mo.

[21] Appl. No.: 331,752

[22] Filed: Oct. 31, 1994

Related U.S. Application Data

[63] Continuation of Ser. No. 959,088, Oct. 9, 1992, abandoned.

[51] Int. Cl.$^6$ .................................................... A61B 5/044
[52] U.S. Cl. ............................................ 128/710; 128/696
[58] Field of Search ................................. 128/696, 702, 128/710, 920; 364/413.02, 413.13, 413.03

[56] References Cited

U.S. PATENT DOCUMENTS

| | | | |
|---|---|---|---|
| 4,292,977 | 10/1981 | Krause et al. | 128/712 |
| 4,628,937 | 12/1986 | Hess et al. | 128/642 |
| 4,697,595 | 10/1987 | Breyer et al. | 128/660 |
| 4,699,147 | 10/1987 | Chilson et al. | 128/642 |
| 4,706,681 | 11/1987 | Breyer et al. | 128/642 |
| 4,797,842 | 1/1989 | Nackman et al. | 364/578 |
| 5,041,973 | 8/1991 | Lebron et al. | 364/413.05 |
| 5,054,496 | 10/1991 | Wen et al. | 128/696 |
| 5,146,926 | 9/1992 | Cohen | 128/710 |
| 5,273,038 | 12/1993 | Beavin | 128/653.1 |
| 5,297,549 | 3/1994 | Beatty et al. | 128/642 |
| 5,311,873 | 5/1994 | Savard et al. | 128/696 |

OTHER PUBLICATIONS

Adam, D.R., "Propagation of depolarization and repolarization processes in the myocardium—An anisotropic model," *IEEE Transactions on Biomedical Engineering* 38: 133–141 (1991).

Harumi, K., et al, "Clinical applications of Electrocardiographic Computer Model," *J. of Electrocardiology* 22 Supp.: 54–63 (1989).

Ideker, R.E., et al., "Simultaneous multichannel cardiac mapping systems," *Pacing Clinical Electrophysiol.* 10: 281–292 (1987).

Ideker, R.E., et al, "The assumptions of isochronal cardiac mapping," *PACE 12*: 456–478 (1989).

(List continued on next page.)

*Primary Examiner*—William E. Kamm
*Assistant Examiner*—Kennedy J. Schaetzle
*Attorney, Agent, or Firm*—Howell & Haferkamp, L.C.

[57] ABSTRACT

An optimal electrophysiologic mapping system for map-directed arrhythmia surgery and cardiac research allows rapid and accurate interpretation of cardiac activation sequences. The system can display activation or potential distribution data on an anatomically accurate 3-D model of the heart and allows fast, interactive control of viewing characteristics, including control of which cardiac surfaces are displayed, control of virtual lighting, rotational control of the displayed image, etc. The system employs two computer programs, GETPIC3 and MAP3, and runs on a Silicon Graphics workstation capable of rapid graphics calculations and displays. The system utilizes 3-D models of epicardial and endocardial surfaces created with the GETPIC3 program from a sequence of 2-D images of a heart. The individual surfaces are triangulated and may be smoothed using a spline function. The MAP3 program displays activation times either as static isochronous maps or as dynamic time-since-last-activation maps. In the latter case, surface color denotes the time elapsed since a particular area activated. Potential distribution data may also be displayed dynamically. A mouse allows the system operator to control real-time rotation of the model in three dimensions, and any surface can be hidden interactively for better viewing of the data. Control is also provided over the starting, stopping, reversing, and repeating of data, as well as over the frame rate for dynamic displays.

40 Claims, 7 Drawing Sheets

OTHER PUBLICATIONS

Laxer, C., et al, "A graphical display system for animating mapped cardiac potentials," abstract, *Proceedings of the Third Annual IEEE Symposium on Computer Based Medical Systems* (1990).

Masse, S., et al, "A three–dimensional display for cardiac activation mapping," *PACE 14:* 538–545 (1991).

Pieper, C.F., et al, "Design and implementation of a new computerized system for intraoperative cardiac mapping," *J. Appl. Physiol. 71:* 1529–1539 (1991).

Simpson, E.V., et al, "Three dimensional visualization of electrical variables in the ventricular wall of the heart," pp. 190–194 in *Proceedings of the IEEE Conference on Visualization in Biomedical Computing* (1990).

Smith, W.M., "Direct cardiac mapping," pp. 849–858 in Zipes and Jalife, eds., *Cardiac Electrophysiology: From Cell to Bedside* (Saunders, 1990).

Tweddell, J.S., et al, "Potential mapping in septal tachycardia: Evaluation of a new intraoperative mapping technique," *Circulation 80 (supp. 1):* I–97 to I–108 (1989).

Palmer, T.C., et al, "Visualization of Bioelectric Phenomena" pp. 429–446 from *High–Performance Computing in Biomedical Research* (T. Pilkington et al, eds., CRC Press, 1992).

May, M. "Supercomputers image the body in three dimensions," *Science* 258: 747 (1992).

MRI or Photographic Image of Heart Cross-section on Computer Screen

Manual Positioning of Vertex Points using Pointer Device

Automated Insertion of Additional Vertices using Splining Algorithm

COMPUTERIZED THREE-DIMENSIONAL CARDIAC MAPPING WITH INTERACTIVE VISUAL DISPLAYS

RELATED APPLICATION

This application is a continuation of U.S. application Ser. No. 07/959,088, filed on Oct. 9, 1992, now abandoned.

GOVERNMENT SUPPORT

The research which led to this invention was supported in part by grants 5R01HL32257 and 5R01HL33722 from the National Institutes of Health.

BACKGROUND OF THE INVENTION

This invention relates to cardiology, cardiac surgery, and computer technology. It provides a slow-motion rotatable visual display, on a computer screen, using three-dimensional surface models, of the depolarization wavefronts on the exterior and interior surfaces of a heart. This computerized depiction is generated by a digital computer with appropriate software, coupled to an electrode array that is direct contacting a beating heart while the patient is under anesthesia. This computerized device, and the visual depictions it generates, allow surgeons or cardiologists to clearly visualize any of several types of heart problems such as arrhythmias, and accurately identify and pinpoint specific areas of damaged or defective cardiac tissue that are causing or aggravating the problem. In some cases, a surgeon or cardiologist can treat and correct the problem, during the same diagnostic operation, by using one or more selected electrodes in the electrode array to ablate specific regions of cardiac tissue which are causing or contributing to the arrhythmia or other problem.

Overview of Myocardial Excitation

The process by which heart cells generate and transmit electrical potentials is discussed in various texts such as *Physiology of Heart and Circulation*, by Robert C. Little (1989) and *Bioelectricity: A Quantitative Approach*, by Robert Plonsey and Roger C. Barr (1988). The following is a brief review of this process.

Before the heart contracts and pumps blood, an electrical event occurs. Each individual heart cell (myocyte) is surrounded by a membrane which separates the intracellular molecules and ions from extracellular molecules and ions. Specifically, the inside and outside of the cells contain four basic ions which contribute to the electrical event: sodium, potassium, chloride, and calcium. The cell membrane is semi-permeable, and the concentrations of ions between the inside and outside of the cell are different. Outside the cell, the sodium, chloride, and calcium ion concentrations are greater than the potassium concentration. Inside the cell, the potassium concentration is much greater. The net result is that if one measures the electrical potential in and outside the cell, the inside of the cell is more negative than outside the cell (−60 to −80 millivolts, mV). To maintain this difference in potential, cells actively transport potassium into the cell and sodium out of the cell, as well as transporting other ions in and out of the cell. Specialized proteins inside the membranes of these cells are responsible for "pumping" the ions in and out of the cell. These are called "ion pumps" and there are a number of these pumps, in addition to the ones listed above.

The difference in electrical potential (voltage) maintained by these pumps is called the "resting potential" of the cell. When a cell is stimulated by some event, such as an electrical stimulus which can be brought about by a external device like an artificial pacemaker or from naturally occurring pacemakers which spontaneously generate electrical potentials in the heart, the cell membrane undergoes a dramatic change (depolarization) such that the membrane allows the external sodium to rush into the cell; after a brief delay, the potassium begins to flow out. Specialized proteins in the cell membrane which allow this to happen are called ion channels. These time-dependent ion channels have a variable conductance which is dependent upon the difference in potential between the inside and the outside of the cell. As the potential increases, it reaches a threshold such that the channels rapidly open, allowing more ions to rush in. After the membrane potential has reached a certain level, this process is reversed and the channels close. Asynchronous activation and deactivation of these ion channels and the ion pumps which then are pushing the ions in and out of the cell return the potential back to its resting potential. This recovery process is called repolarization.

The cardiac myocytes are interconnected with each other by junctions which permit one cell, when it depolarizes, to stimulate the cell next to it by allowing ions to pass between the two cells. This changes the membrane potential of the adjacent cell, bringing it to threshold and resulting in a propagation of the electrical activity and excitation through the tissue.

As the ions move between the inside and outside of the cell, the current generates an extracellular electrical field. This field can be detected on the heart and throughout the body, including on the body surface. This field which appears on the body surface is measured when a standard electrocardiogram (ECG, also abbreviated as EKG) is taken.

There are a variety of heart cell types, each with its own family of ion channels which give that cell type certain characteristics. In the upper two chambers of the heart, the atria, there are specialized myocytes in an area of the heart called the "sinus node." This area acts as the natural pacemaker of the heart. This specialized cardiac tissue spontaneously depolarizes without outside stimulation from other cells. This starts the spread of the excitation wave to other atrial myocytes. These waves propagate at speeds of 0.5–1.0 M/sec. As the waves travel through the heart muscle, each cell goes from a resting state, with a membrane potential of about −60 to −80 mV, to a depolarized state with a membrane potential of about +10 to +20 mV. The moving line of maximum depolarization can be regarded as a wavefront.

The upper two chambers of the heart, the atria, are electrically insulated from the lower two chambers, the ventricles. Another group of specialized myocardial cells, the atrioventricular (AV) node, connects the upper two chambers to the lower two chambers. The AV node then connects to a network of fibers on the inside of the ventricles called the "Purkinje system," which rapidly spreads the electrical signal to the rest of the ventricle, which then activates. Once a cell has undergone a depolarization, this initiates a process of excitation contraction coupling and sets into process the electromechanical event which results in contraction of the cells and heart muscle, which pumps the blood.

Abnormalities in the initiation and/or spread of the electrical wavefront through the heart muscle result in what are called "arrhythmias", or irregular heartbeats. Rapid abnormalities are called "tachyarrhythmias," while slow abnormalities are called "bradyarrhythmias." Both types of arrhythmias can result in abnormal contractions of the heart, which usually decreases the amount of blood pumped to the body.

Additional terms that are widely used to describe heartbeat irregularities include tachycardia (an abnormally rapid heartbeat that stops short of flutter, such as up to about 180 beats per minute), flutter (a very weak heartbeat at an intermediate rate between tachycardia and fibrillation), and fibrillation (a very rapid pulsation that does not generate a true heartbeat and which is ineffective at pumping blood). In general, these and other problems (such as intermittent skipping of heartbeats) can all be regarded as arrhythmias.

Of particular interest to this invention are tachyarrhythmias. Of specific interest in the atria are several atrial tachyarrhythmias which decrease the blood flow from the upper two chambers of the heart to the lower two chambers of the heart. These are: (1) ectopic atrial tachycardia, which results from abnormal pacemakers firing rapidly; (2) atrial flutter, which is the result of a large wavefront which spreads around in a circle, rapidly reinitiating the atrium such that it is unable to pump blood efficiently; and (3) atrial fibrillation, in which multiple circuits of wavefronts rapidly spread in an irregular and disorganized fashion throughout the atrium, greatly decreasing the efficiency of blood transport to the ventricles.

In the ventricle, similar types of tachyarrhythmias can occur which result in ventricular tachycardia, which can be rapidly fatal if the ventricles are unable to pump enough blood to the rest of the body.

Methods for measuring these electrical wavefronts, and for depicting them in a clear and easily-interpreted manner so that they can be medically treated by surgical or other means, is the subject of this invention. By surgical or other intervention using devices such as scalpels or lasers, or by using a radiofrequency emitter as an ablation tool, these tachyarrhythmias can be treated so that the rhythm of the heart is improved and blood is pumped in a more normal and efficient manner.

Cardiac Mapping Under the Prior Art

During the diagnosis and treatment of arrythmias, it would be exceptionally helpful if a surgeon or cardiologist could study and analyze the depolarization waves that are manifested by the passage of electrical signals through the myocardial tissue. For example, in some situations, a bundle of cardiac tissue can effectively short-circuit the normal process of relatively slow conduction from the atria to the ventricles. This disrupts the contraction of the atrial and ventricular walls, reducing the ability of the heart to pump blood effectively.

As another example, ventricular tachycardia is often caused by a "reentry" problem, wherein a depolarization signal travelling through the ventricular myocardial tissue can reenter the ventricular tissue by means of a "short circuit" that bypasses the AV node and causes spurious activation of a second depolarization signal. Frequently, the best treatment for such a problem is to cut through or otherwise kill the cells that are causing the short circuit. However, it is often difficult to pinpoint the cells that are the source of the problem. If a sufficiently accurate mapping technique were available, it would greatly aid in the treatment of such problems.

In order to try to overcome these problems, heart surgeons and cardiologists working with computer specialists have made a number of attempts at so-called "cardiac mapping." In this context, cardiac mapping refers to the acquisition, analysis, and display of data which will reveal the patterns of electrical conduction and depolarization through and around the heart.

One of the first cardiac mapping systems that was developed involved a set of two electrodes. One electrode, referred to herein as a reference electrode, is placed at a single fixed location which remains the same throughout the entire test. The signal from this electrode is recorded using a device such as a strip-chart in an electrocardiograph, or using a digital readout which gives a time for when each heartbeat occurred, as measured at the location of that electrode. The second electrode is manually touched to a number of points around the surface of the heart; this is done by the surgeon during open-chest surgery. The difference (measured in milliseconds) between the reference electrode peak and the second electrode peak is then evaluated in an effort to develop an estimate of how quickly the depolarization wave travels through the myocardium and reaches various parts of the heart. This type of measurement is described in articles such as Gallagher et al 1982.

Despite its limitations, the two-electrode system is still in widespread use. However, multi-electrode systems have been developed at various medical schools for clinicial use, and are commercially available from companies such as Arrhythmia Research Technologies Inc. These systems gather data simultaneously from numerous electrodes which form an array in a non-conducting device. In one such system, described in Pieper et al 1991, techniques developed for printed circuit boards are used to deposit and etch a thin layer of copper on a flexible layer of polyamide. By using etching to control the exposed areas and conductor leads, an array of numerous electrodes is generated on one surface of a flexible plastic strip. These strip arrays are then mounted on a larger holding device. In one such device, ten or more strip arrays are sewed inside a large elastic sock which can be stretched over the outside of a heart, to measure wavefronts which pass across the epicardium. In another type of device, strip arrays are mounted on the outside of an inflatable latex balloon. The balloon is attached to the end of a rigid tube, inserted into an atrial or ventricular cavity, and inflated by filling it with warm saline solution; this allows the electrode strips to measurement wavefronts on endocardial surfaces. Sock-type and balloon-type electrode arrays are described and illustrated in Pieper et al 1991 and in various other articles cited therein, and in U.S. Pat. No. 4,699,147 (Chilson and Smith 1987). U.S. Pat. No. 4,628,937 (Hess and Tarjan 1986) discloses an electrode array mounted in a pliable cup which can conform to various heart surfaces. Other items of prior art, such as U.S. Pat. Nos. 4,697,595 and 4,706,681 (both by Breyer et al 1987) disclose catheter instruments with marking devices that allow the exact location of the instrument to be easily monitored by ultrasonic imaging as the instruments travel through the blood vessels of a patient toward the heart.

The term "template" is used herein to refer to a non-conductive component or assembly which is used to hold multiple electrodes in a spaced configuration in an electrode array. Elastic socks, inflatable balloon devices, and pliable mounting cups are all regarded herein as templates. Flexible polyamide strips which are used to generate strip arrays are also referred to herein as templates. When a template-and-electrode surface is contacted with a heart surface, the non-conductive template holds the electrodes in place while the electrodes measure electrical potentials at a pattern of locations on the heart surface.

Numerous articles (including Gallagher et al 1982, Smith and Ideker 1983, Ideker et al 1987, Tweddell et al 1989, Ideker et al 1989, Smith et al 1990, and Laxer et al 1990) describe cardiac mapping systems referred to herein as "two-dimensional" (2D) systems. In 2D mapping, electrodes and computers are used to generate time-dependent depictions of wavefronts. These 2D depictions are characterized by the fact that they are shown, usually on plotter printouts or color monitors, in the form of flattened partial surfaces.

Although most 2D mapping systems only provide static displays, comparable to a slide projector, the 2D system described in Laxer et al 1990 can provide dynamic displays, analogous to a movie or video.

In 2D systems, the epicardial surface is depicted by planar projections, usually in the form of two roughly circular figures which form a pair. One picture, which is conventionally positioned on the left side of the pair, depicts the front (anterior) portion of an epicardial or endocardial surface. The other picture, on the right side of the pair, depicts the rear (posterior) portion of the same epicardial or endocardial surface. Each heart surface is depicted as though a piece of paper, which was wrapped around the heart during the measuring procedure, is removed from the heart and laid out on a flat surface while it is analyzed. By carefully studying the two side-by-side pictures, a surgeon or cardiologist tries to develop a mental image of the motion of a wavefront which travels around the entire surface, depicted by the two partial images.

Planar projections and 2D mapping systems necessarily lead to major distortions of the complex curved surfaces of a heart. In addition, when two side-by-side projections are used to depict the front and back sides of a heart surface, they require the surgeon or cardiologist to mentally correlate discontinuous isocontours which reach the edge of one surface depiction and jump over to the other surface depiction. Due to the distortions of planar projections, the curvatures that are common in isocontour lines, and other limitations of 2D displays, it is very difficult for a surgeon or cardiologist to develop a good mental image of what is occurring. Surgeons and cardiologists must work extensively with such systems in order to become truly comfortable with them and adroit at interpreting the images they provide.

By contrast, the subject invention involves improved types of displays which are referred to herein as three-dimensional (3D) displays. As the term is used herein, a 3D display involves a depiction of a three-dimensional surface which utilizes accurate measurements in three dimensions (referred to herein as width, height, and depth, using orthogonal coordinates). Even though a 3D display is usually generated and shown on the relatively flat screen of a computer monitor, or printed on a flat sheet of paper using a computerized plotter device, it provides a three-dimensionally accurate image which can be rotated about one or more of the three main axes, on an interactive basis (as described below), thereby revealing surfaces which were hidden from other perspectives. Such images can also be provided with shading using virtual light sources (both direct and ambient, simultaneously) to give the depiction a realistic and easily-interpreted image which is comparable to what a surgeon or cardiologist would see if they were looking at the heart itself under normal lighting conditions.

Two prior publications describe previous efforts to create 3D cardiac mapping systems. Masse et al 1991 uses dots to represent electrode locations. This model does not generate a seperate model of the cardiac surfaces; instead, the locations of the electrodes are used to develop a rough approximation of the surfaces. The dots change in brightness as a wavefront passes. Since different colors are assigned to different classes of electrodes, a surgeon or cardiologist can develop a mental approximation of where the electrodes are located, and of how a wavefront is progressing.

Simpson et al 1990 describes several different software programs, including: (1) the TRICON program, which uses magnetic resonance imaging to generate planar slice images of the heart (MRI), which are then converted into a triangulated surface image; (2) the GSURF program, which displays the surface model generated by the TRICON software, together with the locations of needles and recording electrodes; and (3) the GVOL program, which constructs a volume model of the ventricular walls by creating imaginary cubes between epicardial and endocardial surfaces, and then colors each cube with a hue or intensity that reflects data interpolated from measurements made by nearby electrodes.

The system described in Simpson et al 1990 can produce only static displays; each display can depict data from only a single moment in time. By way of analogy, that system is comparable to using a slide projector to show slides. Each time a picture needs to be changed to show the continuing progress of a wavefront, the previous picture needs to be pulled out and the next picture needs to be loaded into the projector.

By contrast, the subject invention provides a dynamic display, comparable to a movie or video, which shows (in slow motion) the progress of a depolarization wavefront as it passes through the heart. This dynamic display can be viewed and interpreted much more quickly, more easily, and more clearly than a series of static displays, each of which must be loaded into the system one at a time. In addition, a dynamic display can be easily interpreted and used by surgeons or cardiologists who are new to the system and have been through only a single brief training session.

The subject invention also provides a number of features and enhancements which make the system even more useful. For example, the subject invention can depict more than one type of dynamic data on each heart surface. Two highly useful dynamic displays depict (1) time since last activation, and (2) direct electrical potentials. These two different types of maps are usually referred to as "activation time maps" (ATM's) and potential distribution maps (PDM's), and are discussed in detail below. In either type of map, the data can be displayed by assigning a specific color to each of several ranges of numerical values; by watching the movement of the colors, the movement of a depolarization wave can be interpreted easily. In addition, a special procedure is used to ensure that the boundaries between two adjacent colors appear distinct and clear rather than fuzzy.

The computer apparatus described herein can also display dynamic as well as static data on a surface model. For example, a dynamic PDM display can be "frozen" at any moment in time (i.e., the motion can be stopped while the display remains in clear focus on the monitor screen), and numerical data such as mV potentials measured by each electrode can be superimposed on the frozen image. These and other features will be described below.

Accordingly, one object of the subject invention is to provide a computerized system which will allow the dynamic display of electrical wavefronts across a three-dimensionally accurate surface model depiction of a heart.

Another object of this invention is to provide a dynamic 3D mapping and display system which can dynamically depict the progress of depolarization waves across the endocardial and epicardial surfaces of the heart, on 3D surface representations which can be rotated about any orthogonal axis, using a compact computer workstation which can be afforded by any major hospital.

Another object of this invention is to provide a computerized display system which uses colors to depict the movement of depolarization waves across the endocardial and epicardial surfaces of the heart, wherein an enhancement method is provided to ensure that the boundary between two adjacent colors is clear and distinct.

Another object of this invention is to provide a computerized display system which dynamically depicts the motion of depolarization waves across the endocardial and epicardial surfaces of the heart, wherein the moving indicia can be frozen at any point in time and wherein numerical or other static data can be quickly displayed on the frozen image.

These and other objects and advantages will become apparent from the summary and detailed description which follow, and from the drawings.

SUMMARY OF THE INVENTION

A computerized apparatus is disclosed which can visually display the depolarization waves that travel around the heart during each heartbeat, on a three-dimensional surface model which depicts atrial or ventricular epicardial or endocardial surfaces of a mammalian heart. To create the surface model, a method such as fixed tissue photography or magnetic resonance imaging is used to generate two-dimensional horizontal-slice images for numerous horizontal sections spaced slightly apart from each other. Vertices that define the epicardial and endocardial wall surfaces for each horizontal section can be generated manually, using a computerized pointing device. The locations of the vertex points are stored as digitized three-dimensional coordinates. When adjacent vertices are connected, the resulting triangular facets depict the epicardial and endocardial surfaces of each myocardial wall, preferably using multiple hundreds or thousands of facets to closely approximate the curved surfaces of the heart. A resulting model showing, for example, both the left and right atrial interior surfaces can be displayed on a computer screen, showing the left atrial endocardial surface in one color and the adjacent right atrial endocardial surface in a second color. To enhance the three-dimensional appearance of the display, direct and ambient virtual light sources can be defined, and the brightness of each facet will vary depending on the angle between the facet and the direct light source. This generates a lifelike three-dimensional appearance which can be easily understood and interpreted at a glance. The surface model, displayed on a color computer monitor, can be rotated around any axis, under operator control, to provide views from any perspective.

In order to diagnose a patient suffering from a heart problem, an electrode array is constructed which contains numerous electrodes (preferably well over 100 for an epicardial surface) mounted in a non-conducting template. The template is placed in direct contact with the desired cardiac surface during open-chest surgery or using catheters which pass through blood vessels and enter the heart chambers. The electrodes, which have known positions in the template, measure voltage potentials on the heart surface during a measurement period covering at least one complete heartbeat. These measurements are converted into digital data which can be processed by the computer to create a visual display of the depolarization waves that travel across the heart surfaces. These displays can be shown in slow motion on the computer monitor, in any of several manners that can be easily interpreted and understood by a surgeon or cardiologist. For example, to create an activation time map (ATM), a spectrum of colors can be assigned, using red to indicate the depolarization wavefront, followed by other colors (such as orange and yellow) or by colors with decreasing brightness or intensity, to indicate increasing times (in milliseconds) that have elapsed at each location on the heart surface since the passage of a wavefront. Similarly, a potential distribution map (PDM) can be generated which shows voltages at each moment in time. These colors provide an easily interpreted dynamic image of a wavefront passing across a heart surface. These images can be displayed at different speeds, frozen at any point in time while numerical data are superimposed, and manipulated in various other ways. In addition to diagnostic use, the electrodes can be used as treatment devices.

By applying high-frequency voltage to an electrode, the electrode can be converted into a radiofrequency emitter which can function as an ablation tool to kill cells in the vicinity of the electrode.

DESCRIPTION OF THE PREFERRED EMBODIMENTS

Figure 1:
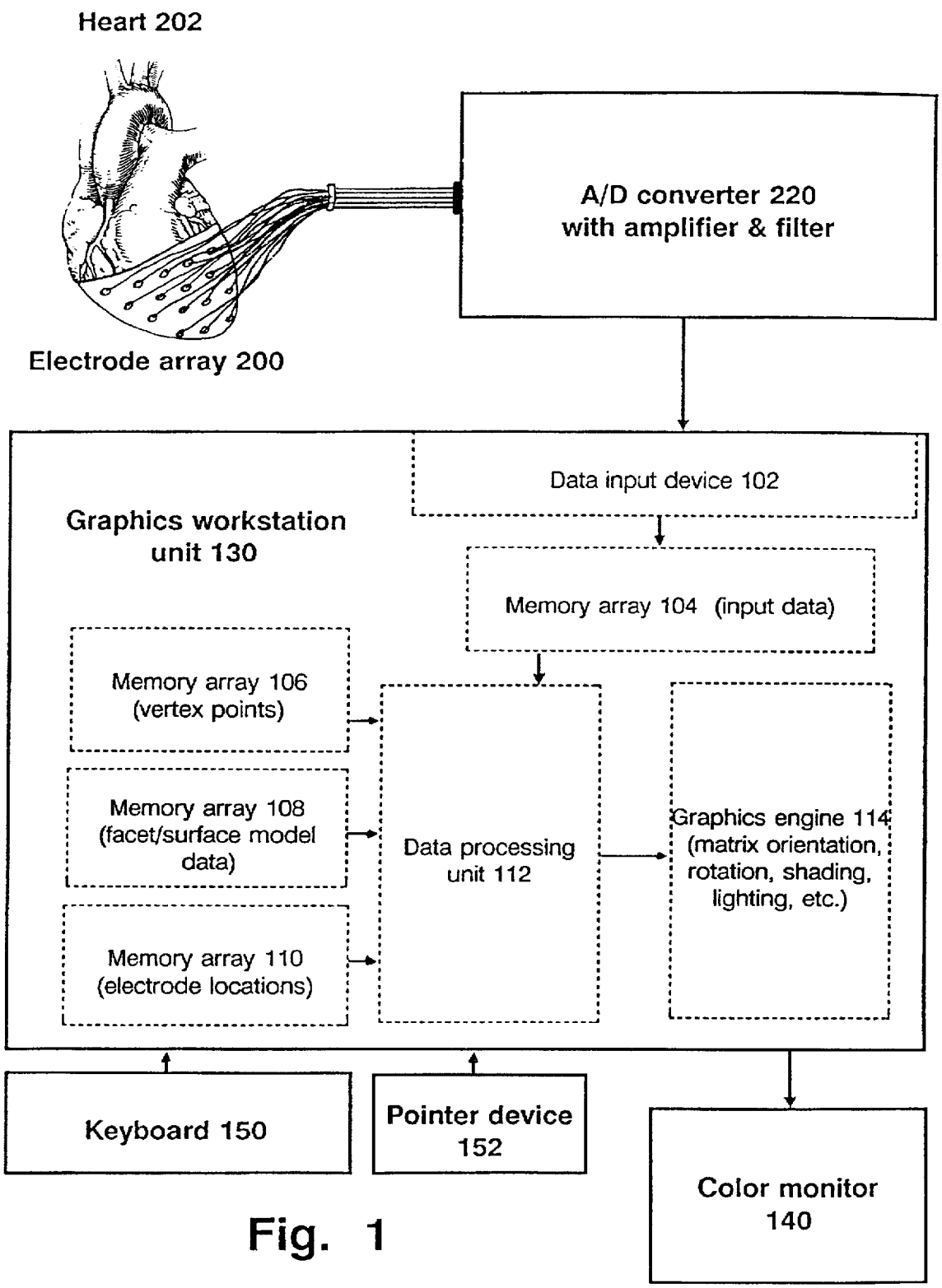
FIG. 1 is a simplified depiction of the computer apparatus of this invention in use, showing the computer processing unit, a color monitor, a keyboard, and a pointer device. The computer apparatus interacts with an electrode array which has been placed on a heart surface, which supplies data to the computer via a multi-channel analog-to-digital converter.

This invention discloses a computer apparatus which generates a visual display of the dynamic motion of depolarization waves that travel across the epicardial and/or endocardial surfaces of a mammalian heart during a heartbeat cycle. In order to generate such a display, a number of pieces of hardware and software must be used in a coordinated manner. FIG. 1 is a simplified depiction of the various hardware components of this invention, in use. The computer apparatus 100 comprises:

(a) a data input device 102, which can receive data from a device such as a multiple-channel analog-to-digital converter 220 and route the data to separate memory locations in a data array;

(b) a first memory array 104 which can temporarily hold input data from a multiple-channel input device, wherein the data from each channel is stored in a separate location in the memory array 104;

(c) a second memory array 106 which can store the coordinates of multiple vertex points which depict at least one and preferably at least three cardiac surfaces;

(d) a third memory array 108 which can store data indicating how the vertex points on a specific surface are connected to each other to create facets which form a surface model;

(e) a fourth memory array 110 which can store coordinates indicating the locations of electrodes in one or more electrode arrays;

(f) a data processing unit 112 comprising circuitry which can process data stored in the first, second, and third memory arrays 104, 106, and 108 in a manner which can interact with graphics display hardware to provide a dynamic display of an activation time map (ATM) or a potential distribution map (PDM);

(g) a "graphics engine" 114 comprising a collection of dedicated graphics display hardware, including specialized graphics-related instructions and algorithms embedded in read-only-memory (ROM) chips, designed to rapidly process data and convert it into visual displays. The term "graphics engine" is widely used among computer specialists as a convenient term to refer to such dedicated hardware, or to a computer which contains such hardware.

The data processor 112 uses the vertex coordinates stored in memory array 106, the facet information stored in memory array 108, and the electrode location information stored in memory array 110, to generate processed information which is supplied to the graphics engine 114. The graphics engine 114 provides various routines and algorithms which generate, and provide interactive control over, various aspects of the visual display, including features such as matrix orientation, rotation of an image, virtual lighting, color palettes, shading, etc. When the processed data emerges from the graphics engine 114, it is displayed as an image (or collection of images) on a color monitor 140, discussed below. The images display a surface model composed of triangular facets (or other polygonal facets, as described below) which depict at least one and frequently two or even three cardiac surfaces.

During a cardiac operation, the motion of depolarizations wavefronts across the cardiac surface(s) is depicted by superimposing information on the facets of the surface model. For example, dynamic displays are depicted by methods such as assigning colors to the facets. At each instant in time, a specific color is assigned to each facet. By sequentially displaying the color assignments for a series of successive moments in time, the data processor 112 and the graphics engine 114 provide a dynamic image which shows the apparent motion of a depolarization wavefront across the facets of the surface model. This dynamic image looks like a slow-motion movie of the depolarization wavefront.

The various memory arrays do not necessarily occupy separate memory devices; they can be generated in different locations in a single large memory unit. In addition, all of the foregoing hardware components can be contained inside a single shell or cabinet, to form a unit referred to herein as a graphics workstation unit 130 (an entire workstation would include the unit 130 along with a keyboard, a pointer device, and a color monitor).

At least two graphic workstations which are specially designed to provide rapid displays of complex graphics on a color monitor are commercially available from Silicon Graphics, Inc. (Mountain View, Calif.). They are the IRIS 4D/320 GTX workstation, and the smaller and less expensive Indigo ELAN system. The subject invention was carried out using the IRIS 4D/320 GTX model, which became available from Silicon Graphics, Inc. first. It is believed that this invention can also be carried out using the Indigo ELAN system, which became available only recently.

It is also possible that this invention can be carried out, in its essential aspects, using even smaller computers, such as workstations available from suppliers such as Digital Equipment Corporation or Sun Microsystems, if those units are provided with integrated circuits (IC's) designed to provide rapid graphics calculations and displays. Such IC's can be installed by methods such as inserting one or more specialized cards containing the desired integrated circuits and supporting circuitry into the expansion slots on a motherboard of a computer designed to carry out multiple non-specific tasks; this type of hardware modification is analogous to inserting a math coprocessor chip and a Super-VGA graphics card into an IBM Personal Computer.

It also appears likely that dedicated graphics cards can be designed which would enable this invention to be carried out on an IBM-type or Apple Macintosh class of desktop computer, if the computer contains a processor such as a 50 megahertz 486 chip from Intel or a faster chip in the 586 class or a future class. The performance of such a unit may be somewhat slower than a larger machine, or it might be limited in other ways; for example, it might be limited to fewer facets to represent each cardiac surface. Nevertheless, the displays that could be generated on desktop machines probably would be adequate for most purposes, and the best system for a particular hospital would be largely a matter of economics.

The output generated by the CPU is displayed on a color monitor 140, which can use a standard cathode-ray tube or other suitable display technology (for example, the 3D displays described herein can be printed on paper using color plotters, to generate color images that can be easily stored for future reference). The monitor screen preferably should contain both (a) a viewing window, which will occupy most of the screen, and (b) a control panel which displays various control options or icons, typically positioned on the left side of the monitor screen. If desired, the monitor screen can also contain a menu or icon bar (which provides pull-down menus or icons indicating specialized routines) and/or a status line (to indicate the names of one or more active files or stand-by files waiting in random access memory) in any desired location, such as across the top of the screen.

The workstation unit 130 and the monitor displays are controlled by a human operator, by means of an alphanumeric keyboard 150 and a pointer device 152 such as a "mouse" or roller ball which causes a cursor-type icon (such as an arrow or pointing finger) to move across the monitor screen. When the moving pointer icon is positioned over a fixed control icon on the monitor screen, a button or other device on the pointer 152 is pressed, which activates a desired operation to generate a change in the display. Various additional control options are also provided, as described below under the heading "User Interactions."

The computer apparatus described above interacts with two other major components that can be fabricated or purchased independently. The first such component is an electrode array 200; the second is an analog-to-digital converter 220.

The electrode array 200 is placed in contact with one or more surfaces of a mammalian heart 202. To reach an endocardial surface without using open-chest surgery, a catheter assembly having a collapsible electrode array mounted on a flexible shaft can be used. The catheter is inserted into a relatively large blood vessel, via an incision through the skin. To reach the right side of the heart, a venous approach is used, typically through the femoral, internal jugular, or subclavian veins. To reach the left side, the femoral or brachial arteries are typically used. The progress of a catheter as it moves through a blood vessel can be continuously monitored on an ultrasound (echolocation) device, and can be controlled by a guiding device that allows an operator to twist the leading end of the catheter in any desired direction as it makes its way toward or through the heart. Alternately, if a patient is undergoing open-chest surgery (i.e., surgery which opens the sternal bone at the front of the rib cage), an electrode array can be placed on the epicardium, or inserted into a heart chamber via an incision made through a myocardial wall.

Based on studies done to date by the Applicants as well as other research teams using prior art systems, it appears that endocardial maps are likely to be sufficient in a large number of cases, and that accompanying epicardial maps will not be required for many patients. If an epicardial map is required, placement of an electrode array on an epicardial surface can be accomplished by means of open-chest surgery. To avoid the need for two operations, the entire graphics workstation described herein can be set up in an operating room during an operation. After the patient's chest is opened, the electrodes can be placed in position on or in the heart, the electrical depolarization data can be gathered, and the data can be processed and displayed on the monitor within a few minutes. This allows a surgeon or cardiologist to precisely locate a tissue lesion or other problem which causes an arrythmia, and then correct it immediately, using means such as a scalpel or laser, or by applying high-frequency voltage to an electrode to convert the electrode into a radiofrequency emitter which functions as an ablation tool.

It should also be noted that various tools for so-called "minimally invasive surgery" (MIS) have been developed for laparoscopic or arthroscopic surgery. In MIS procedures, a fiber optic light source, a miniaturized camera lens, and one or more tools such as forceps, scissors, or biopsy punches are inserted into the abdomen or a joint (such as the knee) of a patient, using slender shafts which pass through relatively small incisions through the skin. Such tools are illustrated in catalogs published by suppliers such as Snowden-Pencer (Tucker, Ga.), Elmed (Addison, Ill.), and Wolf Medical Instruments (Rosemont, Ill.). This approach minimizes post-operative pain, scarring, and internal tissue damage, and it speeds up the recovery of the patient. During the 1980's, minimally invasive cardiac surgery was not developed as intensively as laparoscopic or arthroscopic surgery, due to factors such as the difficulty of closing the pericardium at the end of a cardiac operation. However, efforts are being made to adapt and develop minimally invasive tools and techniques for greater use in cardiothoracic surgery, and such tools can be adapted to the use described herein. For example, a collapsible electrode array such as the pliable cup described in U.S. Pat. No. 4,628,937 (Hess and Tarjan 1986) can be mounted in a rigid shaft, which would be inserted into the chest via a subxiphoid approach while the cup is in a retracted or collapsed configuration. When the cup or shaft reaches the heart, through a slit or window cut through the pericardium, the cup is extended and the array is placed against the ventricular surface of the heart, to perform the measurements necessary to create a ventricular epicardial map.

Various commercially available electrode arrays, such as the sock-type arrays and the balloon-type arrays mentioned in the Background section, can be used as described herein. Alternately, the Applicants have developed electrode arrays which use pliable molded plastic templates and circular bipolar electrodes. Those electrode arrays are described in more detail below, under a separate heading.

In the prototype system developed by the Applicants, an intermediate computer (a VAXstation 3200, sold by Digital Equipment Corp.) was used to analyze, organize, and store the data from the A/D converter, in the form of data arrays, until the arrays could be transferred to a graphics workstation. This was done because the surgical work and the writing of the software was progressing to a fairly advanced state while the graphics workstation was being acquired. In the future, the intermediate computer can be eliminated and the graphics workstation can handle the data analysis, which is described below under its own heading.

The Diagnostic and Treatment Methods of this Invention

In addition to disclosing a computer apparatus, this invention also discloses a method for analyzing and mapping cardiac depolarization activity, for diagnostic purposes (a method is also disclosed for using electrodes as treatment devices). In one preferred embodiment, this method includes the following steps:

(1) A digitized 3D model of a heart surface is loaded into the computer memory. Surface models have been or are being generated, as described below, for canine hearts (which closely resemble human hearts) and for small, medium, and large normal human hearts. Additional models will also be generated in the future for human hearts suffering from a condition called left ventricular hypertrophy, discussed below. Although additional surface models can be generated for any individual patient if desired, using the procedures described below, the models listed above will approximate the size and morphology of nearly all hearts with sufficient accuracy to allow these surface models to be used by a surgeon or cardiologist or cardiologist to analyze and treat arrhythmias in the large majority of cases. Accordingly, in most cases, a pre-existing surface model which approximates the heart of a specific patient can be loaded into the computer memory, without requiring the creation of a surface model from the patient's individual heart.

(2) An electrode array is placed in contact with a selected surface on or in the heart of an animal or patient being analyzed or treated. The locations of the electrodes in the template are known, and are correlated to surface locations in the computerized 3D surface model.

(3) The electrode array is kept in contact with the cardiac surface for a sufficient period of time to gather the desired readings. Typically, the data-gathering period will span at least one complete heartbeat cycle.

If intermittent arrhythmias are being analyzed, the data-gathering period can span any number of heartbeats provided that sufficient memory is available in the computer. Typically, a patient will be continuously monitored using an electrocardiograph (EKG) machine during the entire surgical or catheter procedure. To obtain data on intermittent arrhythmias, the data gathering system can be turned on and left on. When the available memory is full, the most recent data will begin to continuously replace the oldest data. If EKG monitoring indicates that an arrhythmia is occurring, the data gathering process will be continued until the arrhythmia has passed, or until the available memory is nearly full. At that point, the data gathering stops. This technique ensures that a digitized record of the earliest moments during the onset of the arrhythmia will be stored, since those moments are likely to be crucial to diagnosing the arrhythmia.

During the data gathering period, the millivolt potentials that move across the surface of the heart during the transmission of a depolarization wave through the myocardium are measured by the electrodes. Preferably, the analog signals that emerge from the electrodes should be passed through an electronic instrument which can amplify and filter the signals prior to digital processing.

(4) The analog voltage measurements are converted by a multiple-channel analog-to-digital (A/D) converter device 220, described below, into digital data that can be processed by the computer. The data can emerge from the A/D converter 220 in any of several ways, such as in multiple independent channels, or in "multiplexed" form (i.e., as defined fields in a stream of data passing through a limited number of channels). For example, in the multiplexed system used by the Applicants, each A/D converter combined the data from 64 input channels into a single output channel. This allowed 4 converters with single-channel outputs to handle data from 256 electrodes.

(5) The digital data from the A/D converters are analyzed and processed by the computer system, which combines the cardiac measurements with the surface model data and with the electrode position data to generate a time-dependent visual display of one or more depolarization wavefronts passing across the myocardial surface(s) being analyzed.

It is anticipated that this system will normally be carried out by a team of heart surgeons and/or cardiologists working in coordination with at least one computer specialist who has been trained to run the system. The surgeons or cardiologists will open the chest or insert one or more catheters and place the electrode array(s) in position on the heart, and the data will be electronically gathered and analyzed using a portable graphics workstation that can be rolled into an operating room when needed. The computer operator presumably will be operating the computer either in the operating room, or in an adjacent room where the monitor can be seen by the surgeons or cardiologists without leaving the sterile operating suite.

As soon as the measurements from the electrodes become available, the data can be processed and displayed within the space of a few minutes, and the surgeons or cardiologists can see and study the visual displays of the depolarizations waves during the actual operation, while the chest is still open or while the catheter remains in place, without introducing substantial delays or greatly prolonging the amount of time the animal or patient spends under anesthesia or on a cardiopulmonary bypass machine. Upon seeing the displays, which in many cases will indicate the precise location of the heart defect or other problem which required surgery, the electrode array can be removed or retracted and the surgeons or cardiologists can immediately perform an appropriate surgical, laser, or other intervention.

Alternately, the electrode array can be left in position, and the wires coupled to one or more specific electrodes can be coupled to a high frequency voltage supply. This can be done by a method such as (1) uncoupling a multi-lead array connector (which is soldered to the wires leading from the electrodes) from the input port of the A/D converter, (2) transferring the connector to a multi-lead output port attached to an RF energy generator and (3) operating a control knob on the RF energy generator to send voltage to only one (or possibly more) specific electrodes at locations positioned over a tissue lesion which is the source of an arrhythmia problem. The voltage supply will provide a voltage having a desired frequency, typically in the range of about 500 to 700 kilohertz, which will kill cells in direct contact with the electrode or in the immediate vicinity of the electrode; the size of the affected area can be controlled by controlling factors such as the wattage and duration of the RF emission. This provides an electrical means of killing the cells which are provoking the arrhythmia. RF ablation is discussed in various articles such as Haines and DiMarco 1992.

After the intervention has been carried out, the electrode array can be used to take post-treatment measurements. The post-treatment data can be analyzed and displayed, using the same procedures described above, to allow the surgeons or cardiologists to determine whether the intervention was successful and whether additional intervention is necessary.

Files Which Have Been Created and Stored

Several computer files that are relevant to this invention have been stored as follows:

(1) Electronic files containing 3D models of the surfaces of a canine heart have been stored in publicly accessible ("anonymous ftp") electronic files in the Internet system at the Washington University School of Medicine in St. Louis (CTS8.WUSTL.EDU) under two filenames: DOGATR.PIC3, which contains the coordinates of the epicardial and endocardial atrial surfaces from an adult dog weighing about 35 kilograms, and DOGVEN.PIC3, which contains the coordinates of the ventricular surfaces from a similar animal. These spatial coordinates locate the vertices of the small triangles that depict the surfaces of the heart. These files can be copied by anyone with access to the Internet system, and they can be used to construct an identical 3D model of a canine heart. Similar models depicting other types of hearts have been or are being generated using the procedures described below.

(2) An additional file containing the coordinates of the epicardial and endocardial atrial surfaces from an adult male human is stored in the same computer under the filename HUMATR.PIC3. These coordinates were generated as described below, using a photographic technique rather than magnetic resonance imaging.

(3) A listing of the software program used to generate the 3D models of the heart has been stored in the same computer under the directory name GETPIC3.PTO.

(4) A listing of the software program used to process electrode voltage measurements and generate visual displays of cardiac depolarization waves has been stored in the same network, under the directory name MAP3D.PTO.

The HUMATR.PIC3, GETPIC3.PTO, and MAP3D.PTO files are not accessible to the public. If the U.S. Patent and Trademark Office (PTO) decides that access to these files is necessary to enable people skilled in the art to carry out this invention, a listing of the code in those files will be printed out and submitted to the PTO and will become available for public inspection upon issuance of a U.S. patent based upon this patent application. The GETPIC3 and MAP3D software were both written in the C language for an IRIS system sold by Silicon Graphics, Inc.

Both of the software programs, and the canine and human atrial surface model files, are copyrighted and are entitled to copyright protection independently of any patent protection. Unlimited copies can be made of any patent issuing from this patent application; however, the right to copy or distribute an issued patent does not authorize use of the code described in the patent.

Generating Surface Models

As described above, the visual display of a depolarization wave is depicted by imposing time-dependent voltage measurements from a set of electrodes upon a three-dimensional computerized depiction (referred to herein as the 3D model) of the relevant surfaces of a heart. The following section describes how a 3D model is constructed which accurately depicts a particular type of heart.

Several aspects of these models should be recognized:

1. After a 3D model has been generated for a certain type of heart (such as an adult canine heart), it can be used repeatedly, with any number of animals or patients, to analyze and depict the electrical behavior of the hearts of any similar animal or patient. Although the exact shape of the heart of a particular animal or patient may vary in minor details from the 3D model, such variations will be relatively minor and, except in unusual situations, will not substantially alter the visual displays of the depolarization waves in the heart of a specific animal or patient.

2. As mentioned above, surface models have been constructed for both a canine heart and a human heart. Although the hearts of various dogs vary substantially in size (as do the hearts of humans), their shape normally does not. Therefore, even though a range of different template sizes (with corresponding variations in electrode spacings) will be required to accurately gather data from dogs (or humans) having varying sizes, the data from such templates can be displayed on a single surface model, regardless of the size or weight of a particular dog or human. In other words, template sizes will need to be varied, but in most cases, the surface models normally will not.

One possible exception involves a fairly common problem that affects the size thickness of the heart muscle. This problem, called left ventricular hypertrophy (LVH), involves enlargement of the walls of the left ventricle (the main pumping chamber). This problems affects many people suffering from chronic high blood pressure. In addition, the heart of an infant or child may vary sufficiently from the heart of an adult so that the differences are significant with respect to this invention. Therefore, separate surface models are likely to be constructed for human (and possibly canine) hearts suffering from LVH, and for human infants and/or children.

3. Since the atrial and ventricular myocardia are electrically isolated from each other, since each portion of the heart undergoes its own depolarization wave during each heartbeat, and since the great majority of arrhythmia and other such problems originate in one or the other but not both areas, it is preferred to generate atrial and ventricular models which can be handled independently of each other. This allows smaller memory requirements and faster displays on a computer monitor. If desired, it is entirely possible to display the entire epicardial surface (both atrial and ventricular surfaces) in a single coordinated display, using the methods described below; however, since there is little apparent need for such a display, it has not been created by the Applicants.

4. In either atrial or ventricular displays, the system developed by the Applicants allows the simultaneous display of three surfaces: the left and right endocardial surfaces, and the epicardial surface which surrounds both of them. If desired, the epicardial surface can be displayed in a semi-transparent mode without electrical depolarization data, while both of the endocardial surfaces dynamically display depolarization data.

It should also be noted that 3D surface models are superior for this type of use when compared to 3D volume models, which depict the entire heart (including the wall interiors) as a collection of small orthogonal cubes. The benefits of a surface model include:

(1) a surface model requires much less computer memory than a volume model.

(2) the screen displays in a surface model can be altered more rapidly than a volume model, thus allowing rotation with a realistic effect and with little delay.

(3) a surface model offers a better geometric construct upon which to display iso-value contours.

(4) a surface model provides a more anatomically accurate depiction of the surface than most types of volume models. Volume models which try to depict a sloped or rounded surface by means of orthogonal cubes usually generate rough and jagged surface depictions that are more cluttered and difficult to interpret on a computer screen. By contrast, the sloping triangles of a surface model effectively lie flat against the surface of the tissue at any given point, providing a smoother, more accurate, and more easily interpreted display.

Since the data used herein is generated by electrodes that only contact the surface, all of the data is, in effect, surface data. Accordingly, there is no need to develop a model of the entire volume of the heart, and the advantages of avoiding such models are quite important in providing rapid three-dimensional displays in workstations that are available at reasonable cost.

In order to construct an accurate surface model of a particular type of heart, an excised heart from a dog, a human cadaver, or any other desired species is used. If desired, it can be preserved using formaldehyde or any other affixing reagent that does not alter the size and shape of the tissue. In one imaging technique, the heart can analyzed in an MRI scanner in a manner which generates planar images in a series of sections along a chosen axis; this technique was used to create a surface model of a canine heart. The most clear and convenient orientation aligns the Z axis (which is depicted as the vertical axis in most graphs and computer displays) along the long axis of the atrial or ventricular cardiac cavities. During MRI scanning, the heart preferably should be oriented in the scanner so that the X axis (left-to-right in a two-dimensional display) indicates left-to-right orientation in the heart, while the Y axis (bottom-to-top in a 2D display) depicts anterior-to-dorsal in the heart.

In an alternate technique used to create a surface model of the atrial region of a human heart, a heart taken from a cadaver was immobilized in a gel and horizontally sectioned using 3 mm spacing. Each section was photographed, and the photographs were laser-scanned to convert them into gray-scale digitized computer images, which were displayed on a monitor and enhanced using a high-contrast setting. Vertex points were manually inserted and then splined in the same manner described below for the MRI images of canine hearts. Tissue sections can be stained, if desired, to provide even more contrasts between tissue and non-tissue areas, but that was not deemed necessary, and good results were obtained without staining.

Either imaging process (MRI or photographic) will generate a collection of sectional images, where each section is spaced apart by a predetermined distance. Good results have been obtained using images spaced apart from each other by about 2 millimeters (in a canine heart) to 3 mm (in a human heart). Smaller distances between sections provide more facets which more approximate the actual surfaces of a heart more closely; however, they require more memory and more processing time. Spacings of about 2–3 mm for the relatively complex atrial surfaces, and about 5 mm or more for the large and smooth epicardial ventricle surface, are dense enough to provide a good display of a depolarization wave, and the numbers of surface facets available for data display at those spacings are much higher than the number of electrodes used to date. However, the vertical distance between horizontal sections can be decreased to 1 mm or less if desired.

It may be possible to develop a system for using an MRI scanner to generate images of the heart of a patient having heart trouble. The MRI images of the patient's heart can be used either to generate a 3D model of that patient's heart, or to adjust a standard 3D model of a similar heart so that the adjusted model provides a closer approximation than the standard model.

Each sectional image, which is fixed at a particular location on the Z axis, appears as a flat two-dimensional picture when displayed on a monitor screen. The MRI images used by the Applicants were obtained on a Siemens MRI unit (Siemens Medical Systems, Iselin, N.J.) with a 1 tesla coil; the excised heart was placed in a standard-quadrature head coil. This MRI unit generated digital data that were stored on a VAX computer (Digital Equipment Corp., Maynard, Mass.). The scanned image files were copied from the VAX system onto an IRIS 4D/320 GTX workstation (Silicon Graphics, Inc., Mountain View, Calif.) and converted into a Silicon Graphics image file format using a simple routine (entitled "FROMIMA") written in C. This conversion is comparable to converting an ASCI text file from WordStar format into WordPerfect format, and the necessary software can either be purchased as a utility program, or written by any computer scientist who is familiar with the Silicon Graphics, Inc. format requirements.

Insertion of Vertices

When the entire set of MRI images was ready, they were processed as follows. Each image was called up on the monitor, one at a time, where it appeared as a two-dimensional gray-scale black-and-white image. The appearance of these images is comparable to a conventional X-ray, with light grays depicting the walls of the heart and dark grays or black depicting vacant areas such as the interiors of the atrial or ventricular chambers. The boundaries of the myocardial walls, although not as sharp as a black-and-white line drawing, are sufficiently sharp to allow any trained operator to easily determine the location of the wall at any given point within a range of about 1 mm or less.

Using the GETPIC3 software, which was written by one of the co-inventors of this invention, the operator used a handheld electronic mouse to mark a number of points along each epicardial or endocardial surface displayed in the image. As he moved the mouse or other device across a desk-top surface or a mouse pad, a small brightly-colored cursor light moved in a corresponding manner on the screen. When the cursor light reached a target location at the midpoint of a gray transition zone which marked a myocardial surface, the operator pressed a button on the mouse. The computer entered that location as a data point; it recorded the X and Y coordinates, and as the cursor moved away, it left behind a small colored dot to indicate the location of that point. In this manner, the operator could move quickly around the shape of a curve having any shape and mark a series of points on the curve. These points are referred to herein as vertices (a single such point is a vertex). On a computer screen, typical vertices usually ranged from a few millimeters apart (to mark a small, tight curve), up to about a centimeter or more apart (to mark a large or smooth curve).

The vertices were grouped together according to the surface they depicted; for example, the operator would indicate, using the keyboard or monitor control panel, that a certain set of vertices would define the left atrial endocardial surface. The operator would then mark the vertices for that particular surface. These vertices would generate a polygon. After completing the polygon, the operator would indicate to the computer that the next surface (such as the right atrial endocardium) would be marked next, to generate a subsequent polygon.

A relatively small number of vertices (such as about five) were adequate to depict a small circle such as the endocardial surface near an end of an atrial or ventricular cavity, while a much larger number of vertices (such as thirty or more) was used to mark the epicardial surface of the entire heart near the vertical midpoint.

Figure 2A:
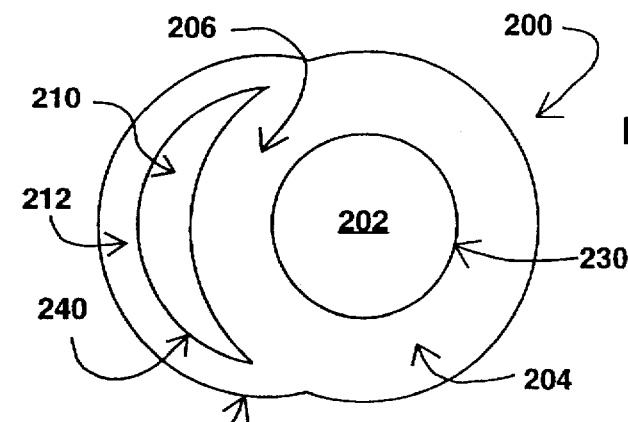
FIG. 2 depicts the construction of three set of vertex points depicting an epicardial and two endocardial ventricular surfaces, using a computerized MRI image of a horizontal section through a ventricular region of a heart.

This initial marking process is depicted, in simplified fashion, in FIG. 2, which is a black-and white drawing depicting a single horizontal section 200 of a canine heart. The MRI image 200, shown in FIG. 2A prior to the addition of any vertices, shows a roughly circular left ventricular cavity 202 bounded by exterior wall 204 and septum 206, and a crescent-shaped right ventricular cavity 210 bounded by exterior wall 212 and the septum 206. The left ventricle is conventionally shown on the right side of a drawing or display, since this is the orientation that would be seen by someone looking at a patient or a heart from the front.

Figure 2B:
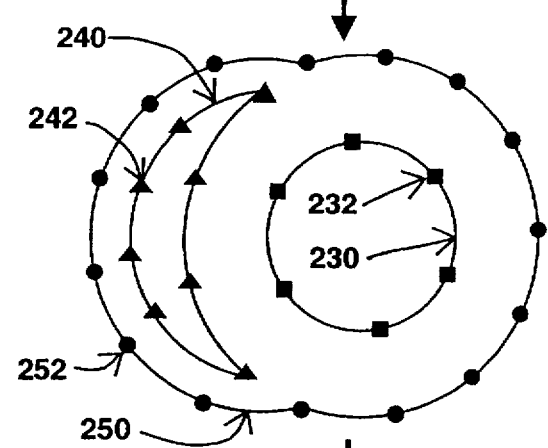

The three cardiac surfaces that are relevant to this invention are:

(1) the left ventricular endocardial surface 230. In FIG. 2B, this left endocardial surface 230 is marked by closed squares 232. These marking points were manually positioned on the image, as described above.

(2) the right ventricular endocardial surface 240, which is marked by closed triangles 242 in FIG. 2B.

(3) the epicardial surface 250 which surrounds the entire heart. This epicardial surface 250 is marked with closed circles 252 in FIG. 2B.

On a color monitor, each surface is marked with different colored vertices. For example, the left endocardial vertices can be blue, the right endocardial vertices can be red, and the epicardial vertices can be yellow. This helps the operator visualize and distinguish each surface on the gray background, and it helps the operator make sure the vertices do not overlap, which otherwise might become a problem in certain regions where atrial walls are thin.

In actual practice, the marking process was not very time consuming. An experienced operator could complete an entire section in roughly a minute. Depending on the size of the heart and the spacing of the sections along the Z axis, an entire set of vertices depicting all of the surfaces in a heart could be completed in about one to three hours.

Figure 2C:
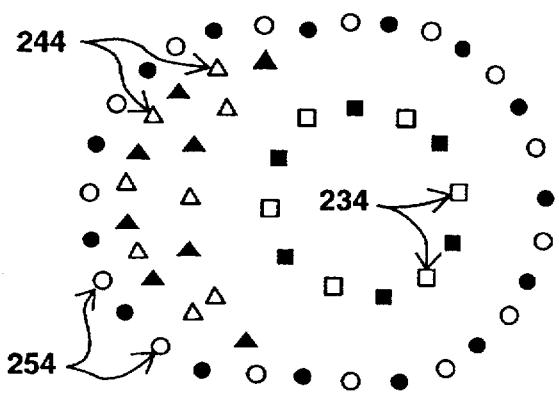

In the next step, which is optional but preferable, each polygon is converted by the computer into a smoother depiction of the curve it represents by means of a mathematical process known as "splining." This process can involve interpolation splining, which preserves manually inserted vertices and adds additional calculated vertices; this process is depicted, in simplified form, in FIG. 2C, where the calculated vertices are represented by open squares 234, open triangles 244, and open circles 254.

Alternately, a different technique called approximation splining uses the manually inserted vertices to calculate a smooth curve, then it creates a set of calculated vertices that are evenly spaced around the curve. This technique discards the original manually inserted vertices, after the new vertices have been generated. When followed by the subsequent processing described below, approximation splining tends to provide more evenly spaced and regular surface facets, so it was used by the Applicants.

Both of these splining techniques are described in various texts such as Newman and Sproull's *Principles of Interactive Computer Graphics* (1979 or later). Splining algorithms are commercially available in most graphics software packages.

After the vertices were established and stored in computer memory, the computer no longer used the MRI images. From that point on, it worked with the digital coordinates that define the vertices.

Determining Triangulated Facets

After vertex points have been defined for all of the horizontal sections in a certain cardiac surface, the next step in constructing the surface model requires imaginary lines (segments) to be drawn between the vertex points in vertically adjacent polygons; for example, the vertices in the polygon that represents a certain atrial epicardial section must be connected, not to the endocardial polygons in the same horizontal section, but to the epicardial polygons in the sections immediately above and below. These imaginary lines will then serve as the borders of triangular facets which closely approximate the actual 3D surfaces of the heart.

The process of selecting optimal segments between two adjacent sections, when each section has multiple vertices, requires an algorithm to determine where the segments should be placed. Depending on the number of vertex points in each of two adjacent cross-sections and their spacing in each cross-section, a number of different ways can be generated to connect the two sets of fixed points to each other, using imaginary lines. It should be borne in mind that two adjacent sections frequently will have different numbers of vertices; for example, as the sections approach the lowest tip of a ventricular endocardial or epicardial surface, one particular section might have 10 vertices while the section immediately below it, which passes through a smaller horizontal cross-section of tissue, might have only 6 or 8 vertices. Furthermore, the vertices will not be lined up with each other vertically between two different sections, since they were initially inserted manually.

This process is depicted in a highly simplified manner in FIG. 3, which indicates a set of triangular facets between two adjacent horizontal sections, shown in perspective, which are designated as the H(n) section on the bottom and the H(n+1) section on top. The variable "n" indicates that a certain section is the nth horizontal section. Sections are conventionally numbered in sequence starting at the bottom of a surface and proceeding toward the top. The (n+1) section is located adjacent to and directly above the nth section.

Figure 3A:
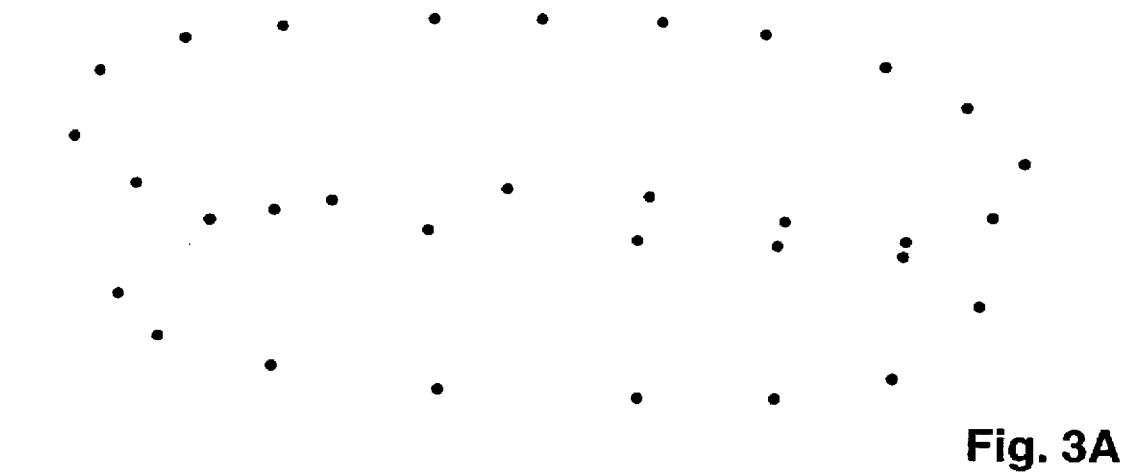
FIG. 3 depicts the creation of a set of triangulated facets between two adjacent horizontal sections.
Figure 3B:
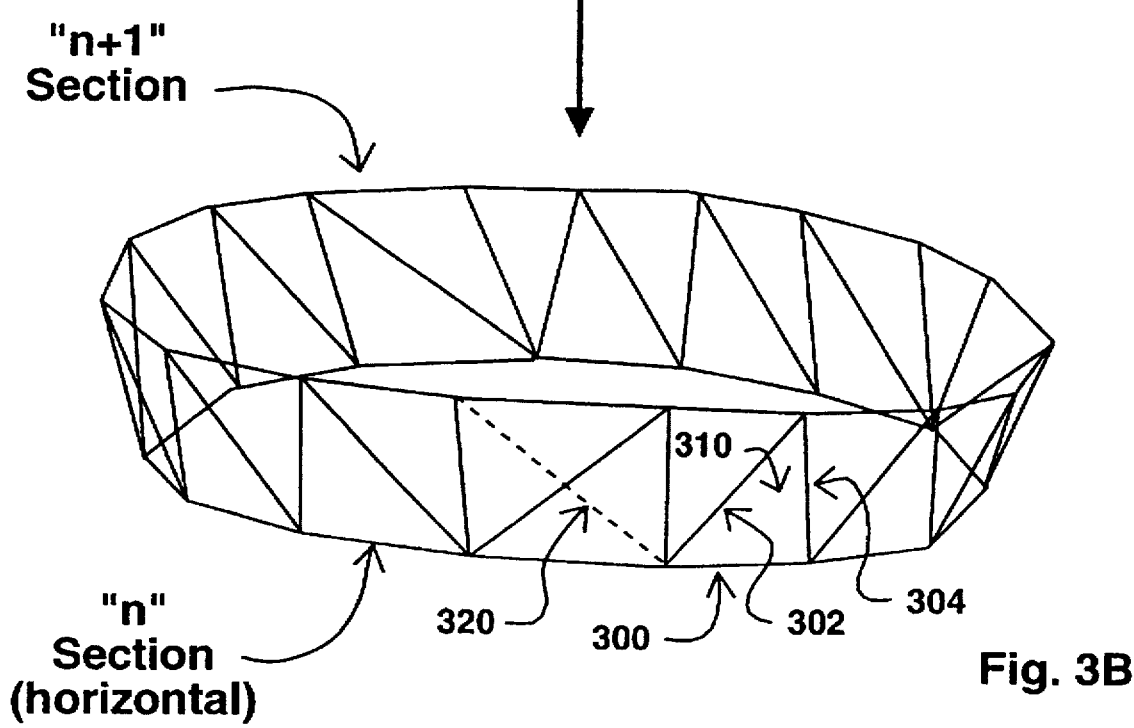

FIG. 3A depicts a set of points in space which represent vertex points, and FIG. 3B depicts one possible set of traingular facets which can be used to model the roughly vertical surface between the two horizontal sets of vertices. Each line segment 300, 302, and 304 is used to connect two vertices; the three segments, together, form the boundaries of a single triangular facet 310. To illustrate the problem generated by multiple possible arrangements of trianglers, a dotted-line segment 320 is also shown which connects two vertex points that would not properly be connected by the minimum-surface area arrangement.

The standard algorithm for determining a minimum-surface-area set of facets based on fixed vertex points is known as the Fuchs algorithm, in honor of the first author of the paper that first described the algorithm (Fuchs et al 1977). This algorithm generates a minimal surface-area model by an iterative process. It uses the digitized data in two arrays, which contain the data from vertex points in two adjacent sections. The H(n) array contains coordinates for the vertices located on the nth horizontal section, while the H(n+1) array contains coordinates for the vertices on the adjacent (n+1)th section.

The Fuchs algorithm generates a minimum surface area arrangement by means of an iterative procedure which can be regarded as a "brute force" method. It generates every possible triangle arrangement and calculates the sum of the areas of the triangles for each such arrangement. It then compares the surface area sums for each of the different arrangements. Eventually, it identifies and selects a set of triangles having the lowest total surface area, which is then stored and subsequently used as the surface model. A computerized routine which carried out that algorithm, written in the C language for use on a UNIX operating system, was initially provided to the Applicants by Ed Simpson of the Duke University (North Carolina) research team; that routine is mentioned in Simpson et al 1990, as part of the GSURF and TRICON programs developed by Simpson et al.

That routine was subsequently modified by the Applicants. Rather than calculating surface area sums for every possible configuration of triangles, the computer routine created by the Applicants works in a simplified manner. When working with two arrays designated as H(n) and H(n+1), as discussed above, it selects the first set of X and Y coordinates in the Hn array and designates those coordinates as P1 coordinates (i.e., they specify the location of the first point, called P1, in the H(n) array). The computer then analyzes the coordinates in the adjacent H(n+1) array and identifies the point in the H(n+1) array which is closest to the P1 point in the H(n) array. That point is then designated as the P1 point in the H(n+1) array. In the next processing step, the coordinates of the newly designated P1 point in the H(n+1) array are shifted, so that the P1(n+1) point will occupy the first position in the H(n+1) array. In effect, this lines up (as closely as possible) the points in the two adjacent arrays before any other calculations are carried out; it shifts (rotates) the position of the coordinates in the array, without changing their linear sequence or the location in space which they represent.

The amended routine used by the Applicants then draws an imaginary line between the first point (the P1 point) in the H(n) array and the first (P1) point in the H(n+1) array. This creation of a first triangle side will substantially reduce the number of possible triangle arrangements that would otherwise have to be created and tested under the Fuchs algorithm. Although it might be possible that some 3D surfaces might somehow slip through the Applicants' routine without providing absolute minimum surface areas which would be identified by the Fuchs algorithm, the routine used by the Applicants is faster and simpler, and it generates completely adequate facets which closely resemble the surfaces of the heart.

These routines were used by the Applicants to generate 3D surface models having roughly 3000 triangular facets in an epicardial atrial surface, and an additional 3000 facets in a combined set of left and right atrial endocardial surfaces. As large numbers of accurately-placed vertices are used to generate small surface triangles, the planar triangles asymptotically approach the actual curved surfaces of the heart and provide a more accurate and more easily interpreted display of the actual surfaces.

Figure 4:
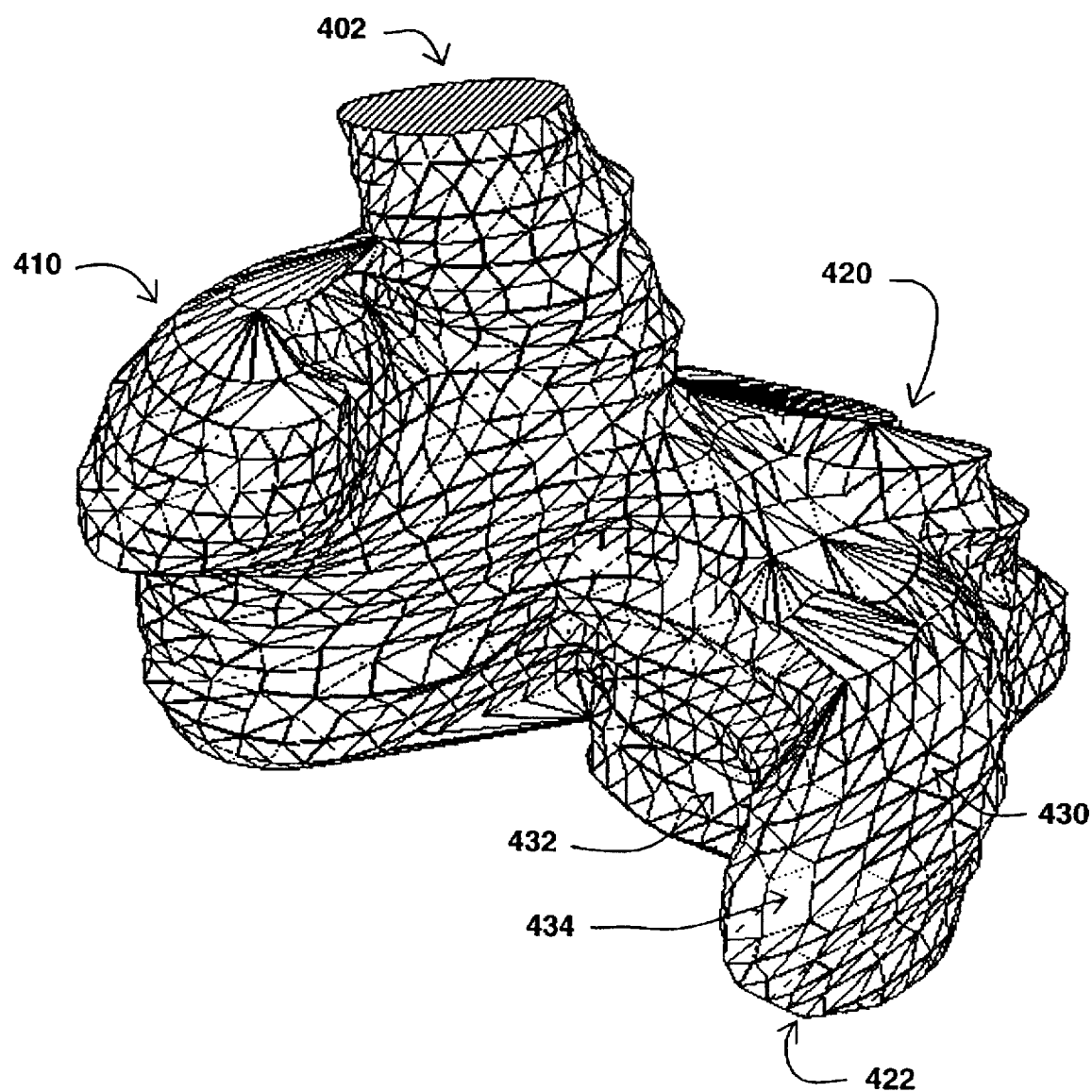
FIG. 4 shows a computer printout of one view of a surface model of the atrial epicardial surface of a canine heart, which indicates that hundreds of triangulated facets can provide a close approximation of the actual heart surfaces.

FIG. 4 shows a computer printout showing a right atrial epicardial surface 400, viewed from the anterior position and slightly above the horizontal. The dark region 402 shows the inlet of the superior vena cava into the right atrium 410; the appendage 422 of the left atrium 420 is also clear in this view. A typical triangular facet is shown by callout number 430. Facets having non-triangular polygonal shapes (such as facet 432), and open spaces such as 434, are artefacts of the image processing routine which was used to convert a color image on a monitor screen into a black-and-white image for printing. The surface model shown in FIG. 4 has roughly 1600 facets; as indicated by the Figure, this is more than enough to provide a good visual approximation of a complex surface. This type of image is much easier to grasp and understand when displayed in color, with virtual light shading, particularly as the observer can see it rotate about an imaginary axis.

The facet data must be stored in a memory array which is independent of the vertex storage array, since it most store data indicating a particular facet configuration. The necessary data on each facet is stored by storing vertex points in a selected sequence, in a counterclockwise manner when the vertices are viewed from outside the surface. Counterclockwise storage enables the computer to calculate a so-called "surface normal vector," which is an imaginary arrow perpendicular to the facet, which points in an outward direction (i.e., from inside the cardiac surface to outside it). By ensuring that the normal vector for each facet points outwardly, the computer can calculate the angle between each facet and a "virtual" direct light source; this light source is used to generate life-like shading of a three-dimensional image, as described below.

Direct and Ambient Lighting

The computer system used by the Applicants displays a 3D surface model which simultaneously uses both direct and ambient lighting. This lighting is often called "virtual" lighting since it does not involve an actual light source. Instead, the operator designates the position of a "virtual" source of direct light, which most commonly is placed in the upper right corner of a viewing screen and in front of the screen, so that it looks as though the image is being lit by a light bulb positioned above and behind the operator's right shoulder as the operator sits at the monitor. The computer then carries out calculations and assigns various color shadings and hues to the surface depiction on the monitor screen, causing the surface model to appear in a relatively life-like manner which is comparable to a solid object in a room lit by a single light bulb.

If the only source of light were a direct light, any surfaces that were not directly exposed to the direct source would appear dark and difficult to decipher, comparable to the unlit side of a half-moon. To avoid that problem, a virtual source of ambient light (also called scattered light) is also provided along with the direct virtual light source.

After the surface model has been generated and the angle of each facet can be calculated, the lighting calculations are carried out by computer instructions which are embedded in the integrated circuits in the platform used by the Applicants. This ensures that they can be carried out very rapidly and will not slow down the display.

Electrodes

There are two major classes of electrodes: unipolar and bipolar.

Unipolar electrodes have a single contact surface and lead-out wire. The voltage at this lead is compared to the voltage at a reference electrode (such as a chest lead, or a Wilson central terminal), to provide a voltage differential that is interpreted as the electrode signal at any instant in time. All unipolar electrodes are compared to the same reference electrode.

Bipolar electrodes have two contact surfaces and two lead-out wires, and the signal they provide is the difference in voltage between the two contact surfaces. Most standard (non-coaxial) bipolar electrodes have two exposed contact surfaces in a side-by-side configuration. Therefore, they are sensitive to the orientation of a wavefront relative to the electrode contacts. If a wavefront is parallel to an imaginary line that passes between the two contact points, the electrode will not see any substantial voltage difference between the side-by-side contact points, regardless of the magnitude of the wavefront. To avoid that problem, bipolar electrodes can have the two contacts in a coaxial configuration; the inner contact occupies a circle in the center, and the other contact occupies an outer ring which surrounds the inner contact. The two contacts are separated by a dielectric (non-conductive) ring. Coaxial electrodes are not affected by the orientation or direction of an activation wavefront.

Figure 5:
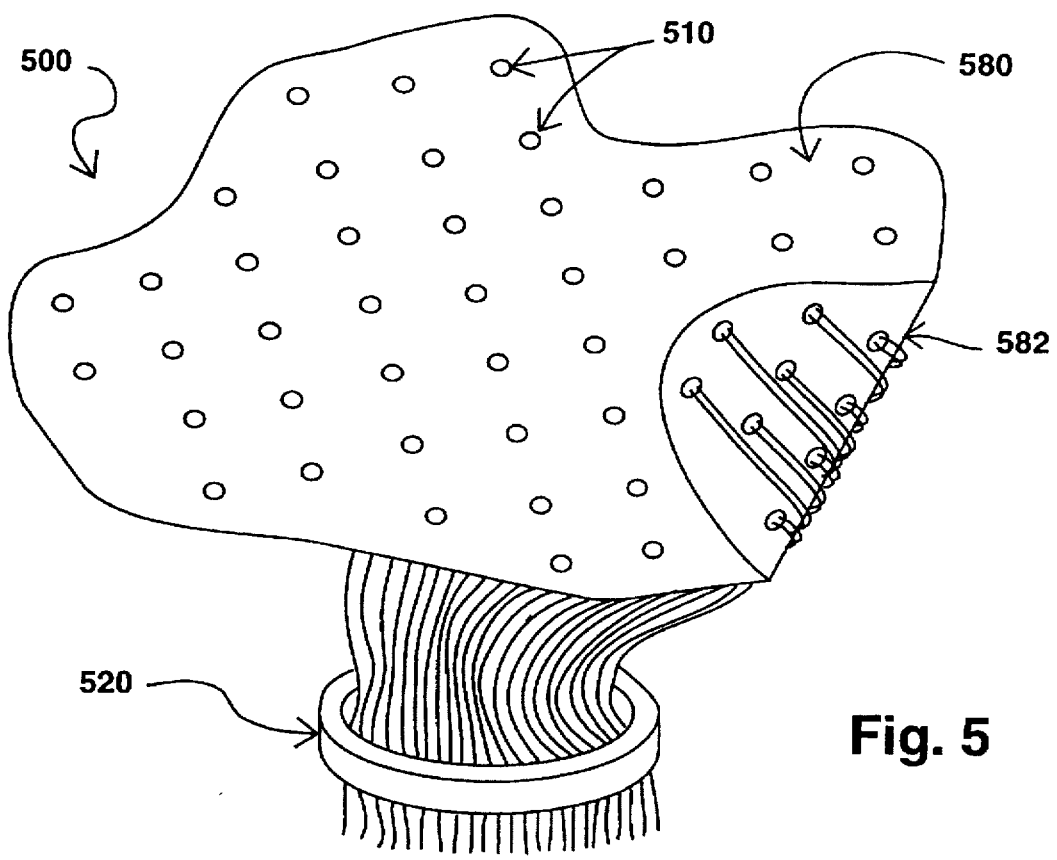
FIG. 5 depicts a flexible molded plastic template used to position and hold multiple bipolar electrodes in an atrial epicardial array.
Figure 6:
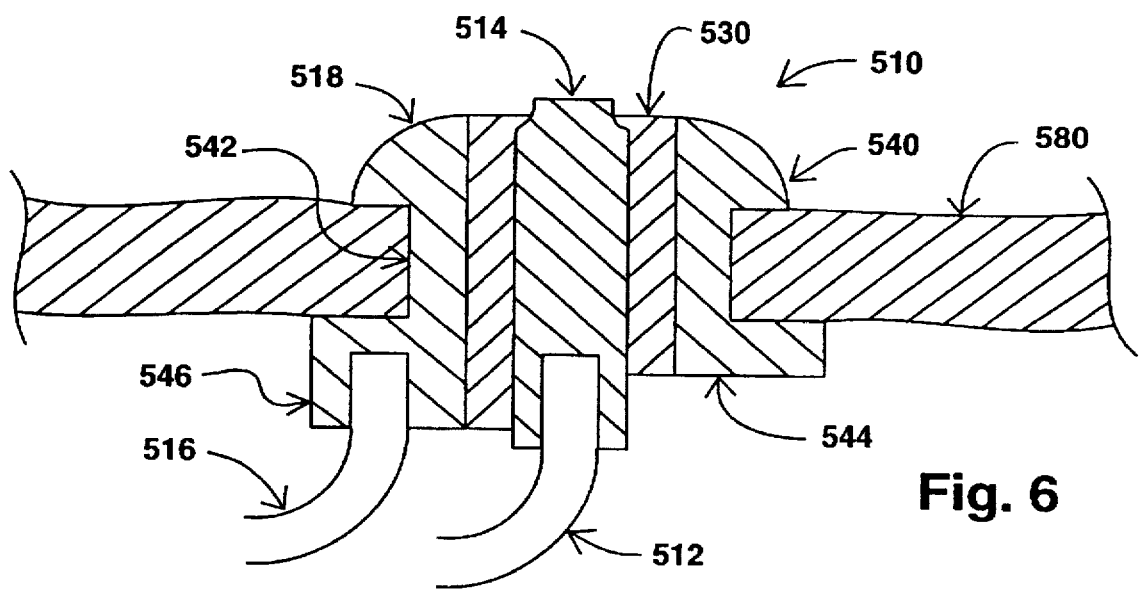
FIG. 6 is a cross-section of a bipolar electrode held by a plastic template.
Figure 7:
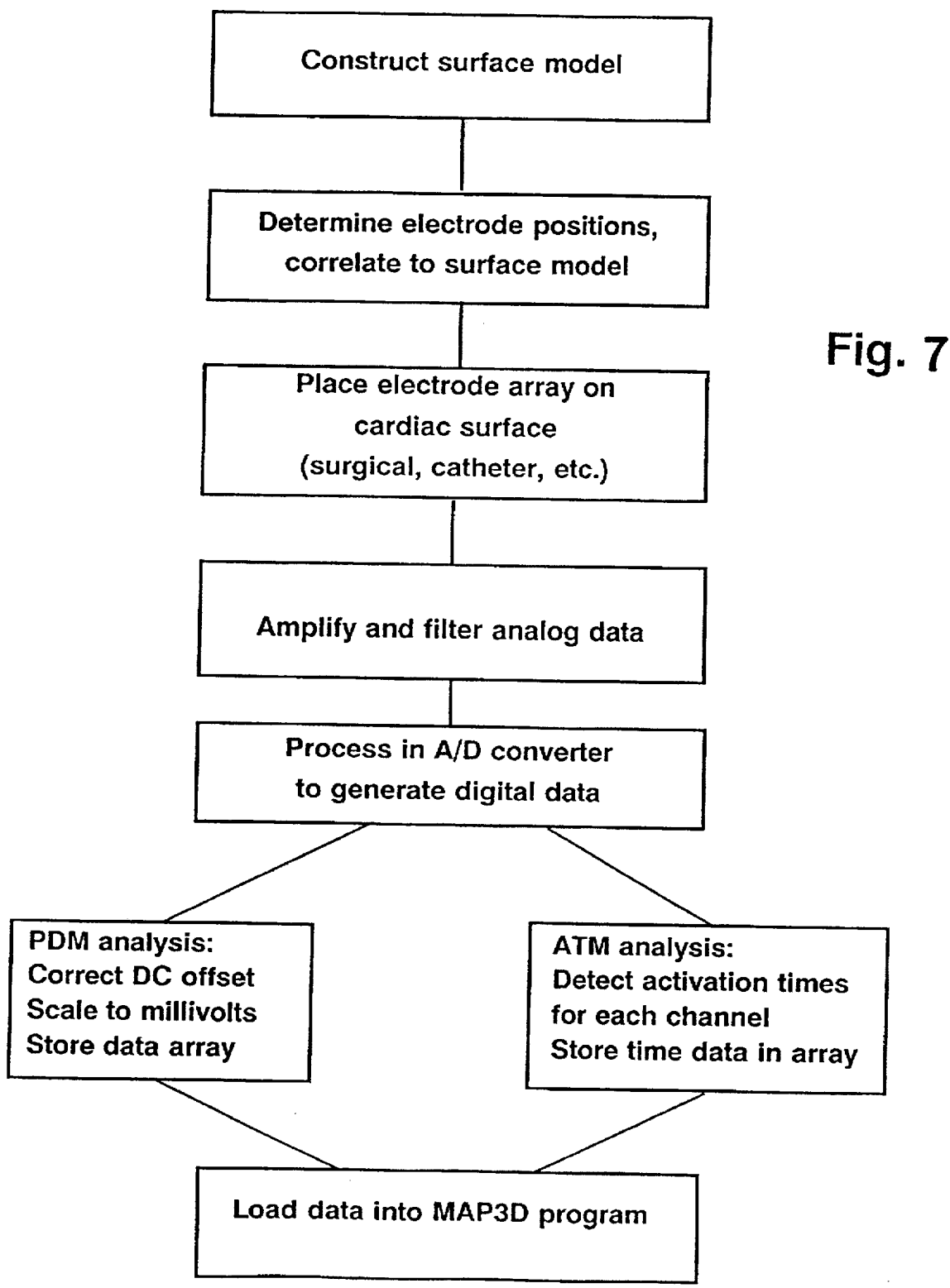
FIG. 7 is a flow chart indicating the major steps in carrying out the invention.
Figure 8:
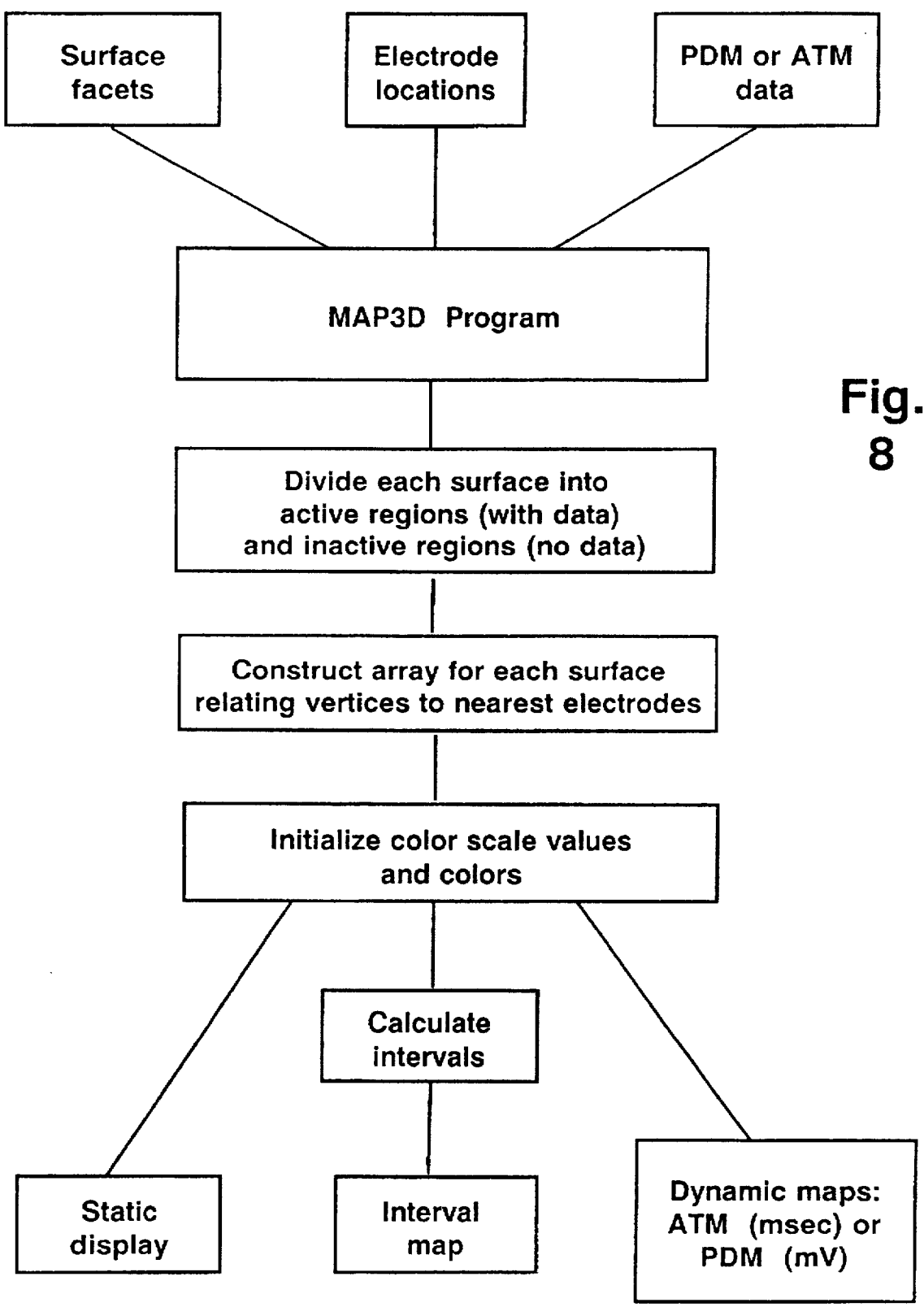
FIG. 8 is a flow chart indicating the various types of data which are compiled and displayed by the MAP3D software.

FIG. 5 depicts one type of electrode array 500 used in the subject invention, having multiple electrodes 510 affixed securely in a non-conductive template 580, as described below. As indicated by the rear view of flap 582, which shows the non-contact side of the array 500, and as shown in FIG. 6, each bipolar electrode 510 has a first wire 512 coupled to the inner contact 514 and and a second wire 516 coupled to the outer contact 518. Each wire is electrically insulated, using plastic or any other suitable insulating material. These wires can be bundled together near the array 500 by means of tape or a plastic band 520 as shown in FIG. 5. The ends of the wires are soldered or otherwise electrically coupled to a multi-lead electronic connector.

FIG. 6 is an enlarged cross-sectional cutaway view of a single bipolar electrode 510, which was designed at the Washington University School of Medicine in St. Louis and initially fabricated by PTI Engineered Plastics, Inc. (Detroit, Mich.). The outer contact 518, which has the shape of a ring, is made of a conductive material which can be molded, such as an alkylbenzylsulfonate (ABS) matrix containing 30% carbon fiber (which is electrically conductive) and 10% stainless steel filler (which makes the electrode opaque and easily visible during ultrasound monitoring). Inner contact 514 is made of the same conductive material. The two contact surfaces are separated and insulated from each other by a non-conductive layer 530 which is made of a material such as ABS which does not contain any conductive filler. This can be accomplished during the molding process if injection molding is used.

The tip of electrode assembly 510 has a head structure 540 (also called a lip) with a diameter of about 2.6 mm, a neck 542 with a diameter of about 1.98 mm, and a base 544 with a diameter of about 3.3 mm. This shape allows each electrode to be held securely in place after the head 540 has been pushed through a flat template layer 580 made of Silastic or other rubberized material, as described below. After passage of the head 540 through a 1.5 mm hole punched at a desired location through the moderately elastic template layer 580, the template layer 580 closes securely around the electrode neck 542. Electrode base 544 is provided with a wire attachment component 546, which can comprise a small projection having a shallow hole with a diameter that can accept the end of a wire.

This is merely one type of electrode array, and other electrode designs and template structures can be used instead. Such alternate electrode arrangements are described in articles such as Pieper et al 1991, which described sock-type and balloon-type arrays, and in U.S. Pat. No. 4,699,147 (Chilson and Smith 1987), which discusses inflatable balloon arrays) and U.S. Pat. No. 4,628,937 (Hess and Tarjan 1986), which discloses pliable cup arrays).

The template/electrode arrays described below are assembled after a template has been made. After the desired number of electrodes were inserted into a template, the exposed metallic leads from a cluster of lead-out wires (which initially were about 60 cm long) were soldered to a multi-lead connector that can be plugged into an electronic data-gathering unit as described below. The Applicants normally used 34-pin electronic cable connectors; each connector handles a cluster of 16 bipolar electrodes.

Unipolar electrodes are simpler, since they require only a single conductive surface with no insulating layers and can be made without requiring procedures such as injection molding. The unipolar electrodes used by the Applicants during their research were made of silver-plated brass beads about 2.2 mm in diameter, having a neck with a diameter of 1.1 mm and a length of 1.1 mm, and a base with a diameter of about 3.05 mm. A 0.33 mm hole was drilled through the base and neck, into the spherical tip. This hole provided a means of securely soldering a lead-out wire to the back of the electrode.

Assembly of a Template/Electrode Array

As mentioned above, a template is the non-conductive component which holds electrodes in a properly spaced configuration. Although an elastic material can be used if desired, elasticity creates problems in controlling and determining exactly where the electrodes contact a heart surface. To minimize such problems during their research, the Applicants used flexible molded plastic templates. These can take any desired shape, such as (1) a contoured layer having a desired shape that allows it to be laid snugly on top of the epicardial surface of the atria; (2) a concave bowl-shaped template that can be fitted around the entire ventricular portion of a heart, so that electrode contact surfaces inside the bowl of the template will contact the epicardial surface of the ventricle wall, or (3) an endocardial template, discussed below.

A contoured shape or molded concave template can be created by spreading an unvulcanized curable material such as a silicone formulation sold under the trade name "Silastic Sheeting" on the outer surface of a "positive" mold of a heart (i.e., a mold having the same external shape and appearance of a heart). Such molds can be made of any moldable compound that can be heated to curing temperatures without degradation; the Applicants normally use a material sold under the trade name "Denstone."

To make such a mold, the cavities of a heart from a cadaver are stuffed with cotton balls to minimize unwanted flexure, then the heart is chemically fixed using an agent such as formaldehyde or glutaraldehyde. After fixation, the heart is placed in a bowl of jelling material, sold under the trade name "Jeltrate Plus." After the Jeltrate cures, the heart is removed from the bowl, which leaves a negative mold of the heart (i.e., a mold having a cavity in the shape of the heart). Denstone is then poured into the negative mold and allowed to harden. The Jeltrate is subsequently removed from around the Denstone, thus leaving the positive mold.

The positive mold should be coated with a compound such as fiberglass resin before placement of the template material on the mold, to ensure that the template material doesn't stick to the mold. If desired, this step can also facilitate placement of ceramic or metallic beads having diameters of about 1 mm on the outer surface of the mold, at precisely determined locations. When the template material is cured, the beads will generate small dimples in the template to indicate where the electrodes should be positioned. This process is facilitated if the template material is placed on the mold in the form of sheets, as compared to spreading a viscous solution across the surfaces. In addition, if applied in the form of sheets, uniform thickness is assured. Despite these advantages of sheets, the material can be applied as a viscous fluid if desired.

The material is then cured by means such as baking to create a template having a fixed but flexible shape.

After a template has been prepared and cured, a punching device is used to punch holes having a desired diameter (such as 1.5 mm). If the dimple approach was used, the holes are punched at the locations indicated by the dimples in the template material.

The construction of an endocardial template mold is less complex, but uses similar compounds and techniques. In making such a mold, the cotton balls used during the chemical fixing process are removed from the cavities and a molding material such as Denstone is injected into each cavity of the fixed heart. After the molding material hardens, the heart tissue is cut away to provide a mold of the cavity. The template is constructed by placing non-cured material on the outside of this mold and then curing the material.

Each template made from such a mold will conform to one of the four heart cavities (left atrial, right atrial, left ventricle, or right ventricle). Each of the cavities has a substantially different shape, so an endocardial template molded for a certain type of cavity can be used only in that type of cavity.

In some situations, the template can be stretched and pulled off the mold without cutting, in other situations, the template is cut and into two pieces which are later glued together. After the initial template formation step, the electrodes and their lead-out wires must be inserted into the inside of the template, so that the contacts will be exposed on the exterior of the template. This can be done in one-piece molds by punching holes in the template at desired locations and then using an finger to push each electrode into the template through a neck-type opening.

After the electrodes have been secured in the mold, a small diameter Silastic tube with a shut off valve on the exposed end is inserted into the cavity, and additional non-cured template material is wrapped snugly around the lead-out wires and the tube. Upon curing, a layer of silicone glue is spread across the neck opening. This generates an airtight template with lead-out wires and a tube for inflation or deflation emerging through a sealed appendage.

The completed electrode-and-template assembly is referred to herein as an electrode array, or simply as an array for convenience (or as an epicardial or endocardial array, when the type of array is important).

An endocardial array can be inserted into a heart cavity through an incision through the wall of a ventricle, or through an atrial appendage, during an open chest operation, or through a catheter, as discussed previously. During the insertion step, the array can be compressed manually, if an open-chest operation is used, and after it enters the cavity, it will return to its original shape due to the elastic characteristic of the template material. When it returns to its molded shape, it presses the electrode contacts (which are exposed on the outer surface of the template) against the endocardial surfaces of the heart cavity. If desired, endocardial templates can also be expanded after insertion, using slightly compressed air or liquid to provide a firmer contact between the electrodes and the endocardial surface.

The foregoing construction was used by the Applicants during their research, but other types of electrodes and templates can be used instead. In particular, techniques have been extensively developed for the construction of printed circuit boards and integrated circuit devices, which involve depositing layers of conductive material in intricate patterns on non-conductive surfaces. Such technology is discussed, for example, in Pieper et al 1991, in which a thin layer of copper was deposited and then etch on a flexible polyamide substrate. By using etching to control the exposed areas and conductor leads, an array of numerous bipolar electrodes was generated on one surface of a flexible plastic strip.

This type of fabrication can achieve a number of goals, including (1) automating and reducing the expense of constructing electrode arrays; (2) increasing the number and density of electrodes in an array, either across the entire surface or at any particular area of interest; (3) increasing the degree of control over the placement of electrodes on a template; and (4) allowing greater control of electrodes on the surfaces of thin deformable plastic strips which can be retracted into and extended out of the shafts of catheters or minimally invasive surgical tools.

Assigning Electrode Locations to the Surface Model

After an electrode array is constructed, the locations of the electrodes must be correlated with a corresponding 3D surface model. This can be done in any of several ways, depending on the particular type of electrode array involved. When using the flexible templates described above, the Applicants used two methods. In the first method, an electrode array was placed in contact with a fixed heart, and an image of the heart and electrode array was generated, using MRI technology. The MRI image was subsequently processed manually, by displaying a heart surface which was in contact with an electrode and then identifying the electrode by examination of the array without the heart. This technique did not work well, due to the metal in the electrodes; however, a similar approach probably can be used with computerized axial tomagraphy (CAT) scanning techniques.

The second approach used by the Applicants involved manual visual estimation. An operator sitting at the computer controls, with the electrode array in one hand and the surface model on the computer screen in front of him, visually estimated the location of each electrode and then used the mouse to specify that electrode location on the surface model. During this process, if the addition of subsequent electrodes indicated that an adjustment of earlier positions was needed, they could be moved by positioning the cursor at a specified electrode locator and then using the mouse to drag the locator to a different position. During initial entry, the electrode locations were entered sequentially and were numbered automatically; if necessary, the numbers could be changed later. As each electrode was entered, the number of the surface triangle it was located on was automatically stored with the electrode number. Although this process was somewhat tedious, it provided adequate results.

Both of these methods were carried out using software routines which are part of the larger GETPIC3 program.

Data Acquisition; A/D Conversion

The signals from the electrodes will be in the range of about −70 to +70 millivolts. Each electrode is connected to an independent analog-to-digital (A/D) channel, and the analog voltage signal from each electrode is passed through an analog amplifier/filter, which amplifies the signal to a level appropriate for an A/D converter and which also provides high and low pass filtering. The high-pass filter cutoff frequency depends on whether unipolar or bipolar electrodes are used (see Smith et al 1990), and the low pass cutoff frequency depends on the desired analog-to-digital sampling rate. Sampling rates of 500 to 2000 Hz have been reported; a sampling rate of 1000 Hz is most widely used.

The prototype data acquisition system, which was assembled by the Applicants, used two PDP 11/23+ modular computer units (sold by Digital Equipment Company, Maynard, Mass.). Each PDP unit contained two A/D converters (DT3362 boards, sold by Data Translation Inc) with 64 input channels and a single multiplexed output channel, a 4 megabyte memory board, and a direct memory access (DMA) interface which allowed the PDP units to tranfer the data to a VAXstation 3200 computer (Digital Equipment Co.). The VAXstation 3200 was used to store and process the data, then the processed files were copied onto the Silicon Graphics IRIS unit described above.

The Silicon Graphics computer was purchased during the course of the project, after a protocol had already been developed for initially processing and sorting the data into arrays and storing the arrays on the VAX system. The Silicon Graphics workstation can handle the entire processing load, if data acquisition hardware and software are loaded into the workstation. This eliminates the need for an intermediate computer between the converter and the graphics workstation.

Data Display

When the surface and electrode models are loaded, each surface is analyzed to determine the area of the surface which will contain data, based on the location of the electrodes on that surface. The limit calculation is based on the maximum of all the minimum interelectrode distances. The user is presented with a two color display of each surface showing the data and non-data areas for that surface. The user may scale the calculated limit to include more or less surface area as data area if desired. The result of this step is to divide each model surface into two regions: an active region, which has depolarization data displayed on it, and an inactive region, which doesn't have depolarization data displayed on it.

A data structure is also generated which contains the index of the closest electrode for each vertex on a surface. This information is used to rapidly assign electrode data values to each vertex. To generate a contour map, the first step is to use the closest vertex data to initialize each surface vertex with the data from the closest electrode.

If desired, an algorithm can be used to assign interpolated data to each vertex, depending on the distance between the vertex and two or more electrodes in the vicinity. For example, if a certain vertex is midway between two adjacent electrodes, it could be assigned a value equal to the average of the values of the two electrodes at any instant in time. However, this would slow down the processing and the graphic display, and in some situations it might distort the display of a progressing wavefront unless steps are taken to detect and account for sharp discontinuities.

The steps to generate a single 3D surface contour map display are the same regardless of whether the display is for a static or interval map (described below), or for one frame of a dynamic (moving) display. There are differences, however, depending on whether a flat-shaded map with distinct contour boundaries or a gouraud-shaded map with gradually changing contour colors (discussed below) is produced.

For activation time maps, a step can be used to detect sharp discontinuities between early and late times, to avoid displaying all possible contours at such discontinuities. It may help to visualize this by thinking of there being an abrupt cliff where elevation changes sharply from a high altitude to a low one. In a topological map it may be appropriate to draw many closely spaced contour lines to represent the elevation change. For an activation time map, however, where an activation wave front contour exists, there are no intermediate times (contours) between that contour edge and the repolarized, high-time value color area it is advancing over. Thus, no intermediate contours should be drawn between the triangle vertex for an area just activated and the other vertices of that triangle which are not yet activated. This discontinuity problem is only present for activation time static maps or time-since-last activation dynamic maps; for potential distribution maps, which are analogous to topological maps, discontinuities do not exist.

Contour Options: Flat, and Gouraud Shading

At least two different approaches can be used to determine the types of boundaries (i.e., the contour lines) between adjacent regions having different values and different colors.

Those two approaches are:

(2) Gouraud-shaded maps. If Gouraud shading is used (Gouraud 1971), the color hues can vary across a single planar facet if the numerical values at the vertex points around the periphery of the facets fall into different color assignment ranges. Gouraud shading effectively interpolates the values across the surface of a facet and displays a smooth continuum of colors accordingly. Due to this type of shading across a single facet, there are no abrupt color discontinuities. The Silicon Graphics GTX workstation is able to perform Gouraud shading calculations using algorithms embedded in integrated circuits, without requiring additional software to be read or used, and the processing is very rapid; a Gouraud shaded surface model having thousands of facets can be displayed at a rate of about 10 frames per second, and the smooth color gradations can provide a visual depiction that is relatively easy to interpret.

However, in some situations, it is desirable to have sharp and distinct boundaries between different colors on the facets. Such boundaries can function in a manner comparable to isocontour lines, and Gouraud shading, which may be helpful when studying an image from a distance, looks fuzzy when the image is analyzed up close. To overcome that problem, a second coloring option has been developed by the Applicants.

(2) Flat-shaded maps. These have distinct contour boundaries between adjacent regions of different color, and a single (i.e., flat) color fills the entire space between successive contour lines; there are no intermediate shades or smooth spectra. In order to generate a distinct boundary between two adjacent flat-shaded areas, an algorithm has been developed by the Applicants which involves dividing triangulated facets into smaller polygons. In this algorithm, each triangle which straddles a contour line is subdivided into two or more polygons by means of lines which bisect the triangle. The locations of the bisecting lines depends on the numerical values at the vertex points of the triangle; the interpolated values are based on an assumed linear distribution between the values at two adjacent vertices on a single triangle. Each polygon which lies within the triangle is then assigned a flat color. The polygons, when combined, completely cover the original triangle. The result, after all the polygons are drawn, is that the data is displayed with distinct contour boundary lines in which one color is on one side of each bisecting line and an adjacent color is on the other side. This display allows the iso-value lines to be observed and aids in determining the speed of the activation wavefront at different points on the surface (fast activation speed is indicated by closely spaced contour lines). These flat-shaded displays cannot move as quickly as Gouraud shaded displays, since they require substantially more calculations. However, the same displays which can be shown at 10 frames per second using Gouraud shading can be shown in the flat-shading method at about 6 frames per second, which is adequate for most purposes, and this algorithm can be embedded in the hardware for faster displays if desired.

Mapping Modes: Static, Interval, and Dynamic

There are several methods of displaying the activation patterns of the heart using the 3D surface depictions provided by this invention. These depictions can be classified as static maps, interval maps, and dynamic maps. These options are referred to herein as "modes," to distinguish this set of options from various other display options (such as options involving flat-shadings versus interpolated or Gouraud shadings, discussed below, and options involving numerical data displayed on the screen).

In general, a static map typically displays data for an entire heartbeat. Static maps are useful for displaying normal rhythms or simple monomorphic arrhythmias. A static map depicts isochronous contour lines. Each contour line represents the position of the activation wavefront at a particular time after some reference time, which usually approximates the entry of the wave into that portion of the heart. On a color display, an isochronous contour map can show the contour lines where the activation front had reached after successive 10 ms intervals (i.e., where the front was located after 10 ms, after 20 ms, after 30 ms, and so on), where each isochronous line is shown in a different color. Any number of colors are available; ten colors have been used to provide easily interpreted displays.

Static maps can also display numerical values, such as numerals positioned adjacent to colored circles indicating electrode locations. Such numerals can indicate both the number of each electrode as well as the data for that electrode at any instant in time.

Interval maps are useful for analyzing complex arrhythmias, such as an atrial fibrillation or a reentrant ventricular tachycardia, where each beat may be different. In an interval map, a number of heartbeats are analyzed to find activation times. The resulting set of times are then analyzed to find a series of intervals in which each interval begins on a beat (activation time) in some channel and only contains one beat in each channel (during a given interval, there may be no beats in some channels). In other words, the interval length is determined by the most rapidly repeating electrode; a new interval begins each time that particular electrode gives a signal indicating that it is commencing another round of depolarization, regardless of whether the entire heart is ready to start a new cycle. This allows interval maps to display arrhythmias, reentry problems, and other problems and irregularities.

Each interval map can be displayed in a manner comparable to a static map, showing isochronous activation contours and numerical values as described above for each interval. A surgeon or cardiologist can study one interval, then click the mouse or keyboard to see the map of the next interval, the preceding interval, or any other selected interval. By studying a series of intervals in sequence, a surgeon or cardiologist can develop a better understanding of the progress, causation, and mediation of a non-monomorphic arrhythmia.

The static maps and interval maps described above can be rotated on the computer screen and viewed from any angle. This is an exceptionally important feature of the subject invention. Most of the prior art cardiac mapping systems only provide two-dimensional maps which cannot adequately display the data in a manner that can be quickly interpreted and understood by a surgeon or cardiologist who does not specialize in interpreting computerized. The benefits of three-dimensional mapping over two-dimensional mapping are discussed in more detail below.

In contrast to static or interval maps, which display fixed isocontours or other data for an entire beat or other interval, dynamic displays (which to the best of the Applicants' knowledge have never previously been achieved by any other system which can provide interactive, anatomically accurate 3D displays) involve motion of color contours or other data on the computer monitor screen, usually in slow motion, which display changes in data during one or more beats. In general, dynamic displays are generated by constructing a set of static maps and displaying the static maps in series, one after the other. Each frame displays data for a particular instant of time. In the Silicon Graphics system used by the Applicants, which involves two 33 megahertz RISC (Reduced Instruction Set Computer) processors and extensive hardware that is devoted exclusively to graphical computation, each static map is constructed "on the fly" rather than prior to commencement of the display. Despite the computational requirements of this system, these displays move in a relatively smooth manner across the computer screen. Unless the surface depiction is being rotated by the operator, there is no motion of the triangular matrix that emulates the surface of the heart. The colors move in increments, but with enough speed and smoothness to provide a clear and easily understandable depiction of the motion of the depolarization wavefronts.

One type of highly useful dynamic display is an activation map which shows, in slow motion, the progress of a depolarization wavefront across a heart surface. For example, a spectrum of colors can be assigned, using red to indicate the depolarization wavefront, followed by orange, yellow, green, and blue to indicate increasing times (in milliseconds) that have elapsed at each location on the heart surface since the passage of the wavefront. This set of colors provides an easily-interpreted moving visual image of the wavefront passing across the heart surface. This depiction can be rotated on the computer screen and viewed from any angle. It can be displayed with electrode numbers if desired, at different speeds, or frozen at any point in time with or without exact numerical values displayed at electrode locations.

Activation time maps (ATM's) are generated as follows. The data from each electrode are analyzed to determine the activation time at each electrode; as described above, this determination will depend on whether the electrodes are unipolar or bipolar (bipolar electrodes usually measure peak voltages, while unipolar electrodes usually measure the rate of change, dv/dt). The activation times in the various channels are used to construct a two-dimensional numerical matrix, with a row for each channel (electrode), and a number of columns equal to the number of milliseconds in the period being analyzed. A highly simplified example of an ATM array is provided in Table 1, to indicate how the data are arranged. For each channel, successive column values are set to the scale maximum, until the column corresponding to the first activation time in that channel is reached. The value in the column for that time is set to zero. Thereafter, the value in each successive column is incremented by one millisecond until the next activation time is reached. The column value is set to zero again, and the process is repeated for each activation in the channel.

For each channel, the resulting numerical matrix contains the time-since-last-activation at each millisecond. These arrays can then be displayed dynamically on the 3D surface model by assigning each vertex on the 3D model to the value of its nearest electrode at each point in time. The resulting colors will effectively show the advancing activation wavefront as an abrupt color change from a high value color (indicating, for example, that more than 100 milliseconds have passed since the last depolarization wavefront passed) to a low value (e.g., a red color indicating that a wavefront passed that particular electrode within the last 10 ms). The area around each electrode will then pass through the series of assigned intermediate colors (such as orange if a wavefront passed by within 10 to 20 ms, yellow for the 20 to 30 ms range, and so forth). These intermediate colors which will follow behind the advancing wavefront will indicate how long has elapsed since the wavefront passed.

Another way to display data using dynamic mapping is referred to as potential distribution mapping (PDM). In this method, the data in each channel is displayed as a voltage relative to a baseline value, which is usually treated as zero. The facets that surround each electrode are displayed in a color that corresponds to a voltage (potential) range at that electrode, at or during the time period which is being evaluated. A dynamic PDM display can be frozen at any desired moment in time to show the voltage distributions across a heart surface at a single instant.

In a PDM display, the temporal spacing of the frame data can be each A/D sample interval, or some multiple of the sample interval. For example, if the A/D sampling rate is 1000 Hz, each frame can represent the voltage data for a single millisecond, or for any desired number of milliseconds.

Unipolar electrodes normally are used to collect PDM display data; however, bipolar electrodes can be used if the voltage from a single lead (preferably the internal lead if a co-axial bipolar electrode is used) is isolated and compared to the reference electrode.

User Interactions

The software created by the Applicants provides a number of control options which provide immediate user-interactive control over the viewing orientation and over the data which is displayed on the monitor screen. These levels of control greatly enhance the usefulness of the invention in helping surgeons and cardiologists rapidly and clearly interpret the data. In particular, it allows surgeons and cardiologists to study the progress of a depolarization wave around an entire cardiac surface, even though the surfaces (atrial endocardial surfaces in particular) have complex and irregular shapes. The invention accomplishes this goal by allowing the image to be rotated in real-time (i.e., the image rotates in a smooth and continuous manner, without jumping discontinuously to different images, and without being limited to a limited number of previously prepared views), and by allowing the display of a wavefront to be started, stopped, frozen, and reversed at any moment in time, until the progress of a wave across each surface of interest, at each relevant moment in time, has been displayed and studied to the satisfaction of the surgeon or cardiologist.

The subject invention provides these capabilities in a manner which is easy for an operator to carry out. For example, the user can rotate the surfaces in any of the three mapping modes, in real time, by a simple procedure using a standard two- or three-button computer mouse. The pointer arrow or other cursor icon on the monitor screen is moved to any location in the viewing window on the monitor screen, and the left button on the mouse is depressed. This causes rotation of the image about an imaginary axis which passes through the center of the image, perpendicular to the location of the pointer icon. For example, if the pointer icon is placed on either side of the cardiac surface image and the mouse button is held down, the image will rotate about an imaginary vertical axis; if the pointer icon is placed directly below the cardiac surface image and the mouse button is held down, the image will rotate about an imaginary horizontal axis. In each situation, the previously hidden perspective which is close to the location of the pointer arrow will become visible as that portion of the surface rotates to the center of the image.

In addition, these rotational options are not limited to orthogonal axes. For example, if the pointer icon is placed in the lower right corner of the window screen, the image will rotate about a diagonal imaginary axis which passes from the lower left corner to the upper right corner of the viewing screen.

In addition, rotation can also be provided about an imaginary axis perpendicular to the monitor screen; this causes the image to rotate in a clockwise or counterclockwise manner. This is controlled by a different button on the mouse (the middle or right button, depending on what type of mouse is used).

The rate of rotation can also be controlled quite easily. If the pointer icon on the monitor screen is placed near the edge of the model image (i.e., near the center of the viewing window), the image will rotate fairly slowly. If the icon is placed near the outside of the viewing screen (farther away from the surface image), the image will rotate more rapidly.

These rotational options allow simple, relatively rapid rotation of the image so that the surface can be studied closely from any desired angle for any desired period of time. Furthermore, rotation of the image is not limited; if the pointer button is held down continuously while the pointer arrow is in the viewing window, the image will continue rotating in complete circles any desired number of times.

In another type of interactive control procedure, a pointing device can be used to load a certain type of data into active memory, or to commence a certain type of data processing operation, or to alter the parameters of the display (for example, to initialize or change the assignment of colors, using a color pallette). This is usually done by moving the pointer arrow to an icon indicating what type of operation will take place, or what type of data is stored in the memory, and clicking the pointer button.

Various other options can also be provided if desired. For example, a pointer device could be used to access pull-down menus listed horizontally on a single line across the top of the monitor screen. These menus indicate various options available to an operator. When not in active use, the pull-down menus disappear, which leaves the screen uncluttered. In yet another option, a pointer device can be used to transfer or otherwise move data or an icon from one location to another, using a "dragging" operation; the pointer arrow is placed on a desired icon, the button is pressed and held down, and the pointer arrow is moved to a different location while the button remains depressed.

All of these pointer-controlled operations are conventional and are familiar to anyone who uses computers equipped with pointing devices. Along with control operations carried out using a keyboard, they are referred to herein as "interactive" controls. The operator (which is used herein to refer to a human who is operating the computer controls) directs the computer to create or carry out a desired calculation, procedure, display, or other operation, and the computer responds either immediately, or within the time required to carry out the necessary calculations and generate the display. In an interative control system, the human operator can observe any changes in the display which result from a control activity, and can then make further adjustments or direct the computer to carry out additional procedures based on the observed results.

The user can also selectively hide or display any surface. For example, to simulate what would be seen if the electrical waves across the heart surface could actually be watched by an observer, the surfaces of the 3D model can be rendered opaque, so that only the surfaces on the side toward the viewer will be visible at any given time. Alternately, an epicardial surface shown on a display can be made semi-transparent, allowing both epicardial and endocardial surfaces to be visible at the same time.

Any dynamic display can be stopped (frozen) at any desired time and started again when desired, by means such as clicking a mouse button or other key. The frame rate can also be adjusted between 1 and 10 frames/sec, either by means of a fixed setting, or by slowing down the advancement of a display by holding down a mouse button. In addition, a time bar is provided in the display, and the display can be started at any desired moment by moving the pointer icon to the desired position in the time bar and clicking the mouse.

In general, a display will be shown in a large rectangular window which occupies most of the computer screen, while a menu is provided on one side of the screen (such as on the left quarter of the screen). The menu will contain various commands such as "Stop," "Start," and "Reverse" and a variable spped control can be provided by means of a sliding icon. A command is executed by manually moving the mouse on the mouse pad or desktop until the cursor on the screen reaches the desired command, then clicking the mouse button on that command.

The Benefits of 3D Depictions

Although several two-dimensional (2D) mapping systems have been previously described, there are a number of major advantages of three-dimensional (3D) displays compared to 2D displays.

In general, it is much easier for a surgeon or cardiologist to quickly and accurately interpret a 3D mapping system (particularly a dynamic display) without requiring extensive training or practice to learn how the system works and to develop a level of skill and reliability in using the system. By way of analogy, a trained histologist who specializes in analying tissue sections, MRI scans, and CAT scans can gradually learn to recognize and interpret subtleties that non-specialists would not notice or understand. However, doctors who specialize in cardiac surgery or cardiology, as a rule, do not also specialize in interpreting tissue samples; the disciplines of histology and surgery require substantially different skills and practice, and virtually no one is a true specialist in both. Accordingly, if a new type of computerized display can offer surgeons and cardiologists a substantial advantage, by displaying data in a clearer and more quickly and easily understandable manner, such a display system provides a major advantage in the speed of acceptance and use, and in the accuracy and reliability of the intervention decisions that are based on such displays.

This factor is magnified and multiplied in cardiac surgery, since the necessary decisions and interventions must be made while a patient remains under anesthesia (and, frequently, on a cardiopulmonary bypass machine), and since many arrhythmias are complex and irregular and are much easier to diagnose if a dynamic display is available.

The 3D mapping system described herein is a major advance over prior art mapping techniques, since it facilitates the rapid and accurate interpretation of activation patterns by any surgeon or cardiologist who has been through a single training session to become familiar with the types of displays that are available. The anatomy and topology of the heart (particularly the atrium) are highly complex; however, a 3D model permits a surgeon or cardiologist to easily visualize electrophysiological data on the same anatomic structure that he sees in the operating room. By contrast, a 2D display necessarily distorts the anatomy and therefore the overlayed data contours.

In addition, in any effort to display front and rear views simultaneously, while using a 2D mapping system, it is necessary to predetermine a view of the surface and split the surface into two parts. This introduces artificial boundaries at the edges of the two parts of the display. Thus, contour lines intersecting the edge of the front view must be mentally connected to the corresponding contour lines at the corresponding edge of the rear view. This is not a simple feat, since most contour lines are neither simple nor straight. These problems are especially acute for atrial displays.

By using a 3D display, the problems of 2D distortion, discontinuity, and having to mentally connect discontinuous curving contour lines are minimized or completely avoided. The entire surface can be viewed by the use of interactive "real-time" rotation of the model. In this context, the phrase "real-time rotation" indicates that if the proper mouse or keyboard control is activated by an operator, the 3D display will rotate in a smooth and continuous manner, displaying the intermediate depictions at every step of the rotation. This gives the appearance of actual rotation, where the frame of reference and the visual image are never disrupted. By contrast, if a system involved, for example, rotation in large jumps, such as 90 degree increments, a surgeon or cardiologist would have to study each new image long enough to reestablish his or her bearings and orientation amd make sure he/she is looking at the heart from the intended angle.

Accordingly, the construction of a 3D surface model showing every surface of a heart allows precise determination and simple, rapid visualization of the location of any aberrant conduction pathways.

Thus, there has been shown and described a new, rapid, and clinically useful computerized device for generating improved slow-motion rotatable visual displays of the depolarization wavefronts on the surfaces of a heart. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Fuchs, H., et al, "Optimal surface reconstruction from planar contours," *Communications of the ACM* 20: 693–702 (1977)

Gallagher, J. J., et al, "Techniques of intraoperative electrophysiolic mapping," *Am. J. Cardiol.* 49: 221–240 (1982)

Gouraud, H., "Continuous shading of curved surfaces," *IEEE Transactions on Computers* C-20(6): 623–629 (June 1971)

Haines, D. E. and DiMarco, J. P., "Current therapy for supraventricular tachycardia," *Current Problems in cardiology* 27: 411–477 (1992)

Ideker, R. E., et al, "Simultaneous multichannel cardiac mapping systems," *Pacing Clinical Electrophysiol.*10: 281–292 (1987)

Ideker, R. E., et al, "The assumptions of isochronal cardiac mapping," *PACE* 12: 456–478 (1989)

Laxer, C., et al, "A graphical display system for animating mapped cardiac potentials," pages 197–204 in *Proceedings of the Third. Annual IEEE symposium on Computer Based Medical Systems* (IEEE Service Center, Piscataway, N.J., catalog number 90CH2845-6, 1990)

Mallet, R., "Discrete smooth interpolation," *ACM Transactions on Graphics* 8: 121–144 (1989)

Masse, S., et al, "A three-dimensional display for cardiac activation mapping," *PACE* 14: 538–545 (1991)

Newman, W., and Sproull, R, *Principles of Interactive Computer Graphics* (McGraw Hill, New York, 1979)

Pieper, C. F., et al, "Design and implementation of a new computerized system for intraoperative cardiac mapping," *J. Appl. Physiol.* 71: 1529–1539 (1991)

Simpson, E. V., et al, "Three dimensional visualization of electrical variables in the ventricular wall of the heart," pages 190–194 in *Proceedings of the Conference on Visualization in Biomedical Computing* (Institute of Electrical and Electronics Engineers, 1990)

Smith, W. M. and Ideker, R. E., "Computer techniques for epicardial and endocardial mapping," *Prog. Cardiovasc. Dis.* 26: 15–32 (1983)

Smith, W. M., "Direct cardiac mapping," Chapter 88 (pages 849–858) in Zipes and Jalife, eds., *Cardiac Electrophysiology: From cell to Bedside* (Saunders, 1990)

Tweddell, J. S., et al, "Potential mapping in septal tachycardia: Evaluation of a new intraoperative mapping technique," *Circulation* 80 (*supp. I*): I-97 to I-108 (1989)

We claim:

1. A digital computer for displaying dynamic motion of depolarization waves across mammalian heart surfaces as detected by an electrode array having multiple electrodes for contacting the heart surface, the digital computer comprising:

a data input device for receiving input data from the multiple electrodes in the electrode array;

at least one memory array for storing data;

means for correlating data from each electrode with a position of contact between that electrode and the heart surface;

digital processing circuitry for generating for each electrode a time-dependent record during at least one heartbeat of depolarization states at the electrode's position of contact with the heart surface;

a color monitor;

means for displaying on the color monitor a three-dimensional surface model of at least one endocardial or epicardial mammalian heart surface, the surface model comprising facets defined by vertex points stored in at least one memory array as three-dimensional coordinates, wherein the facets approximate an endocardial or epicardial heart surface being contacted by the electrode array; and means for generating and displaying, superimposed upon the three-dimensional surface model shown on the color monitor, a dynamic activation map which provides a slow-motion depiction of a depolarization wavefront moving across the heart surface that was contacted and measured by the electrode array, the generating and displaying means including means for assigning colors to facets of the three-dimensional surface model at each moment in time, the assigned colors indicating how many milliseconds elapsed during a heartbeat since depolarization began at an area of tissue on the heart surface which corresponds to that facet on the surface model.

2. The digital computer of claim 1 further comprising a control mechanism that enables an operator to freeze the dynamic activation map at a selected moment in time.

3. The digital computer of claim 2 wherein the control mechanism includes means for an operator to superimpose digital data indicating numerical values measured by individual electrodes at the selected moment in time upon the three-dimensional surface model of the heart at locations corresponding to locations of electrodes in the electrode array.

4. A digital computer for displaying dynamic motion of depolarization waves across mammalian heart surfaces as detected by an electrode array having multiple electrodes for contacting the heart surface, the digital computer comprising:

a data input device for receiving input data from the multiple electrodes in the electrode array;

at least one memory array for storing data;

means for correlating data from each electrode with a position of contact between that electrode and the heart surface;

digital processing circuitry for generating for each electrode a time-dependent record during at least one heartbeat of depolarization states at the electrode's position of contact with the heart surface;

a color monitor;

means for displaying on the color monitor a three-dimensional surface model of at least one endocardial or epicardial mammalian heart surface, the surface model comprising facets defined by vertex points stored in at least one memory array as three-dimensional coordinates, wherein the facets approximate an endocardial or epicardial heart surface being contacted by the electrode array; and means for generating and displaying, superimposed upon the three-dimensional surface model shown on the color monitor, a dynamic potential distribution map which provides a slow-motion depiction of a depolarization wavefront moving across the heart surface that was contacted and measured by the electrode array, the generating and displaying means including means for assigning a color to a specific facet of the three-dimensional surface model at a specific moment in time to indicate a depolarization potential, in millivolts, at an area of heart tissue corresponding to the specific facet.

5. The digital computer of claim 4 further comprising a control mechanism that enables an operator to freeze the dynamic potential distribution map at a selected moment in time.

6. The digital computer of claim 5 wherein the control mechanism includes means for an operator to superimpose digital data indicating numerical values measured by individual electrodes at the selected moment in time upon the three-dimensional surface model of the heart at locations corresponding to locations of electrodes in the electrode array.

7. A digital computer for displaying dynamic motion of depolarization waves across mammalian heart surfaces as measured by a cardiac electrode array having multiple electrodes, the digital computer comprising:

a color monitor;

a data input device for receiving multiple-channel or multiplexed input data gathered by the cardiac electrode array;

a first memory array for storing three-dimensional coordinates for vertex points correlating to at least one cardiac surface, and for storing data indicating how the vertex points are connected to form facets that approximate the cardiac surface;

a second memory array for storing data correlating locations of the multiple electrodes to locations of facets stored in the first memory array;

a third memory array for storing input data gathered by the cardiac electrode array;

a data processing system, which includes a set of software instructions, for compiling data stored in the memory arrays, and for interacting with the color monitor to display a three-dimensional surface model of at least one cardiac surface and to display, in the form of an activation time map, movement of a depolarization wavefront across the three-dimensional surface model to provide a slow-motion depiction of a depolarization wavefront moving across the heart surface measured by the cardiac electrode array, wherein the surface model comprises facets which approximate the cardiac surface, wherein colors are assigned to facets of the three-dimensional surface model at each moment in time, and wherein colors assigned to a specific facet at a specific moment in time indicate how many milliseconds elapsed during a heartbeat since depolarization began at an area of tissue on the heart surface which corresponds to that facet on the surface model; and a control mechanism for rotating the three-dimensional surface model about at least one axis.

8. A digital computer for displaying dynamic motion of depolarization waves across mammalian heart surfaces as measured by a cardiac electrode array having multiple electrodes, the digital computer comprising:

a data input device for receiving multiple-channel or multiplexed input data gathered by the cardiac electrode array;

a first memory array for storing three-dimensional coordinates for vertex points correlating to at least one cardiac surface, and for storing data indicating how the vertex points are connected to form facets that approximate the cardiac surface;

a second memory array for storing data correlating locations of the multiple electrodes to locations of facets stored in the first memory array;

a third memory array for storing input data gathered by the cardiac electrode array;

a color monitor;

a data processing system, which includes a set of software instructions, for compiling data stored in the memory arrays, and for interacting with the color monitor to display a three-dimensional surface model of at least one cardiac surface and to display, in the form of a potential distribution map, movement of a depolarization wavefront across the three-dimensional surface model to provide a slow-motion depiction of a depolarization wavefront moving across the heart surface measured by the cardiac electrode array, wherein the surface model comprises facets which approximate the cardiac surface, wherein colors are assigned to facets of the three-dimensional surface model at each moment in time, and wherein colors assigned to each facet at each moment in time indicate depolarization potentials, in millivolts, at each area of heart tissue corresponding to each facet of the surface model; and a control mechanism for rotating the three-dimensional surface model about at least one axis.

9. A computer-implemented method of treating a cardiac arrhythmia in a patient, which comprises the use of a (1) a digital computer comprising a data input device, memory arrays, digital processing circuitry, and a color monitor, (2) interacting software, (3) an electrode array which has multiple electrodes and which is initially coupled to the digital computer, and (4) a voltage supply which is adjusted to supply, to any selected electrode in the electrode array, a controlled voltage useful for killing myocardial cells in a limited region of heart tissue adjacent to the selected electrode, in order to ablate a selected region of cardiac tissue which contributes to the cardiac arrhythmia, by steps comprising:

a. placing the electrode array in contact with a cardiac surface of a beating mammalian heart, wherein the electrode array is electronically coupled to the data input device of the digital computer which contains, in one or more memory arrays, data used to generate a three-dimensional surface model of the cardiac surface, said surface model comprising facets defined by vertex points which are stored in the computer as three-dimensional coordinates, wherein said facets approximate the cardiac surface, and wherein each electrode in the electrode array has a known position in the electrode array which correlates to a known position on the three-dimensional surface model stored in the computer;

b. using the digital computer to process data from the electrode array to generate and store a time-dependent record of cellular depolarization states on the cardiac surface as measured by the electrodes in the electrode array;

c. using the digital computer to display, on the color monitor, the three-dimensional surface model of the mammalian heart;

d. using the digital computer to generate and display a slow-motion dynamic depiction of cellular depolarization states, superimposed upon the three-dimensional surface model displayed on the color monitor, wherein the dynamic display of the cellular depolarization states provides a slow-motion depiction of a depolarization wavefront moving across the cardiac surface being contacted by the electrodes;

e. visually inspecting the dynamic depiction on the color monitor to identify at least one area of tissue on the cardiac surface which is contributing to an arrhythmia which afflicts the patient's heart;

f. identifying a selected electrode which is located in closest proximity to the area of tissue on the cardiac surface which is contributing to the arrhythmia;

g. using the electrode array, after it has been coupled to the voltage supply, to generate current through the selected electrode, wherein the current which passes through the selected electrode kills myocardial cells located in close proximity to the electrode.

10. The method of claim 9, wherein the electrode array is placed in contact with a heart surface by means of a medical procedure selected from the group consisting of:

a. open-chest surgery;

b. inserting a catheter assembly having a collapsible electrode array mounted on a flexible catheter shaft into a blood vessel and inserting the flexible catheter shaft through the blood vessel until the electrode array reaches the heart; and, c. inserting a minimally invasive surgical tool having a collapsible electrode array mounted on a shaft into a patient's chest via a thoracic epidermal incision.

11. A computer-implemented method for displaying cardiac activation data for a mammalian heart, the method comprising the steps of:

generating an anatomically accurate, three-dimensional surface model of at least one surface of a mammalian heart;

processing activation data collected for a heart of a mammalian subject; and displaying the processed activation data on the three-dimensional surface model under operator control.

12. The method of claim 11 wherein the generating step includes retrieving a series of cross-sectional images of a mammalian heart, constructing polygons by designating vertices that outline surface boundaries in each cross-sectional image, determining the surface to which each polygon belongs, and triangulating the polygons for each surface to thereby construct the three-dimensional surface model.

13. The method of claim 12 wherein the generating step further includes splining each polygon before triangulation.

14. The method of claim 11 wherein the activation data is collected with an electrode array, the method further comprising the step of selectively displaying a plurality of electrodes of the electrode array and their corresponding data on the three-dimensional surface model.

15. The method of claim 11 wherein the displaying step includes statically displaying isochrone data.

16. The method of claim 15 wherein the displaying step further includes statically displaying multiple beat isochrone data in a sequence of time intervals.

17. The method of claim 11 wherein the displaying step includes displaying the three-dimensional surface model using virtual lighting.

18. The method of claim 17 wherein the generating step includes generating a plurality of normal vectors for the three-dimensional surface model, and the displaying step includes adjusting the virtual lighting for the three-dimensional surface model based on angles between the normal vectors and a virtual light source.

19. The method of claim 11 wherein the displaying step includes displaying the activation data on the surface model using gourand-shading.

20. The method of claim 11 wherein the displaying step includes displaying the activation data on the surface model using flat-shading.

21. The method of claim 11 wherein the displaying step includes dynamically displaying the activation data.

22. The method of claim 21 wherein the displaying step further includes computing each frame of the dynamic display in real time.

23. The method of claim 21 wherein the displaying step further includes selectively starting, stopping, reversing, or repeating the dynamically displayed activation data.

24. The method of claim 21 wherein the displaying step further includes dynamically displaying potential distribution data.

25. The method of claim 21 wherein the displaying step further includes dynamically displaying time since last activation data.

26. The method of claim 11 wherein the displaying step includes selectively hiding a surface of the three-dimensional model for more clearly displaying the activation data.

27. The method of claim 11 wherein the generating step includes generating a three-dimensional surface model having an epicardial surface and an endocardial surface at least partially hidden by the epicardial surface when displayed, and the displaying step includes selectively displaying the epicardial surface semi-transparently to thereby display the epicardial and endocardial surfaces simultaneously.

28. The method of claim 11 wherein the displaying step includes selectively rotating the surface model in real time and in any combination of three dimensions.

29. A programmed computer for displaying cardiac activation data for a mammalian heart, the programmed computer comprising:

means for generating an anatomically accurate, three-dimensional surface model of at least one surface of a mammalian heart;

means for inputting activation data collected for a heart of a mammalian subject;

means for processing the input activation data; and means for displaying the processed activation data on the three-dimensional surface model under operator control.

30. The programmed computer of claim 29 further comprising means for a computer operator to rotate the surface model in real time and in any one or more of three dimensions.

31. The programmed computer of claim 30 wherein the displaying means includes means for dynamically displaying the processed activation data.

32. The programmed computer of claim 31 further comprising means for a computer operator to start, stop, reverse, or repeat the dynamically displayed activation data.

33. The programmed computer of claim 32 wherein the input activation data was collected with an electrode array, and the displaying means includes means for selectively displaying electrodes of the electrode array and corresponding data on the surface model.

34. The programmed computer of claim 32 wherein the displaying means includes means for dynamically displaying potential distribution data.

35. The programmed computer of claim 32 wherein the displaying means includes means for dynamically displaying time since last activation data.

36. The programmed computer of claim 32 further comprising means for dividing each surface of the generated surface model into active and inactive regions based on whether activation data was collected therefor.

37. The programmed computer of claim 32 wherein the displaying means includes means for selectively hiding a surface of the three-dimensional surface model to more clearly display the processed activation data.

38. The programmed computer of claim 32 wherein the generated surface model includes an epicardial surface and an endocardial surface at least partially hidden by the epicardial surface when displayed, and the displaying means includes means for selectively displaying the epicardial surface semi-transparently to thereby display the epicardial and endocardial surfaces simultaneously.

39. The programmed computer of claim 30 wherein the displaying means includes means for statically displaying isochrone data.

40. The programmed computer of claim 39 wherein the displaying means includes means for statically displaying multiple beat isochrone data in a sequence of time intervals.

* * * * *